(12) United States Patent
Brown et al.

(10) Patent No.: US 9,101,693 B2
(45) Date of Patent: Aug. 11, 2015

(54) CELL-INDEPENDENT FABRICATION OF TISSUE EQUIVALENTS

(75) Inventors: Robert Brown, London (GB); Showan Nazhat, London (GB); Vivek Mudera, London (GB); Mike Wiseman, London (GB)

(73) Assignee: UCL BUSINESS PLC, London (GB)

( * ) Notice: Subject to any disclaimer, the term of this patent is extended or adjusted under 35 U.S.C. 154(b) by 2139 days.

(21) Appl. No.: 11/631,288

(22) PCT Filed: Jul. 5, 2005

(86) PCT No.: PCT/GB2005/002631
§ 371 (c)(1),
(2), (4) Date: Aug. 14, 2007

(87) PCT Pub. No.: WO2006/003442
PCT Pub. Date: Jan. 12, 2006

(65) Prior Publication Data
US 2008/0131473 A1 Jun. 5, 2008

(30) Foreign Application Priority Data
Jul. 5, 2004 (GB) .................................. 0415080.1

(51) Int. Cl.
*A61L 27/52* (2006.01)
*A61L 27/24* (2006.01)
*A61L 27/38* (2006.01)

(52) U.S. Cl.
CPC .................. *A61L 27/52* (2013.01); *A61L 27/24* (2013.01); *A61L 27/38* (2013.01)

(58) Field of Classification Search
None
See application file for complete search history.

(56) References Cited

U.S. PATENT DOCUMENTS

| | | | | |
|---|---|---|---|---|
| 3,968,567 A | * | 7/1976 | Nevins | 433/224 |
| 4,689,399 A | | 8/1987 | Chu et al. | |
| 4,772,419 A | | 9/1988 | Mälson et al. | |
| 5,756,350 A | * | 5/1998 | Lee et al. | 435/325 |
| 6,174,333 B1 | * | 1/2001 | Kadiyala et al. | 623/11.11 |
| 6,666,886 B1 | * | 12/2003 | Tranquillo et al. | 623/2.42 |
| 7,029,689 B2 | * | 4/2006 | Berglund et al. | 424/423 |
| 7,521,231 B2 | * | 4/2009 | Germain et al. | 435/325 |
| 2002/0106625 A1 | | 8/2002 | Hung et al. | |
| 2002/0159982 A1 | | 10/2002 | Bonassar et al. | |
| 2004/0054372 A1 | | 3/2004 | Corden et al. | |
| 2006/0014284 A1 | | 1/2006 | Graeve | |
| 2006/0273279 A1 | | 12/2006 | Kaplan et al. | |

FOREIGN PATENT DOCUMENTS

| EP | 1 273 312 | 9/2006 |
|---|---|---|
| WO | WO 97/11724 | 4/1997 |
| WO | WO 97/45071 | 12/1997 |
| WO | WO 00/09179 | 2/2000 |
| WO | WO 02/051463 | 7/2002 |
| WO | WO 02/062961 | 8/2002 |
| WO | WO 03/080141 | 10/2003 |
| WO | WO 2005/046457 | 5/2005 |
| WO | WO 2006/003442 | 1/2006 |
| WO | WO 2006/042287 | 4/2006 |
| WO | WO 2006/115892 | 11/2006 |
| WO | WO 2007/060459 | 5/2007 |

OTHER PUBLICATIONS

British Search Report issued in connection with related UK Application No. GB0717168.9, dated Apr. 4, 2008.
British Search Report issued in connection with related UK Application No. GB0713079.2, dated Mar. 18, 2008.
International Search Report issued in connection with related PCT/GB2006/004414, dated Mar. 20, 2008.
Takamatsu et al, "Viability of Deformed Cells", Cryobiology 39, 243-251 (1999).
D'Lima et al, "Human chondrocyte apoptosis in response to mechanical injury", Osteoarthritis and Cartilage (2001) 9, 712-719.
Kurz et al, "Biosynthetic response and mechanical properties of articular cartilage after injurious compression", Journal of Orthopaedic Research 19 (2001) 1140-1146.
Collins English Dictionary 2007 (HarperCollins Publishers, Glasgow, UK), p. 504.
Castro de Garcia et al "Intracellular trehalose improves osmotolerance but not desiccation tolerance in mammalian cells" FEBS Letters 487 (2000) 199-202.
Brown et al "Ultrarapid Engineering of Biomimetic Materials and Tissues: Fabrication of Nano- and Microstructures by Plastic Compression" (2005) Adv Func Mater 15 1762-1770.
International Search Report of PCT/GB2005/002631, mailed Dec. 23, 2005.
Born et al, "Estimation of Disruption of Animal Cells by Laminar Shear Stress", Biotechnology and Bioengineering, vol. 40, pp. 1004-1010 (1992).
Mardikar et al, "Observations on the Shear Damage to Different Animal Cells in a Concentric Cylinder Viscometer", Biotechnology and Bioengineering 68:697-704, 2000.
Kamaraju et al, "Modeling shear-induced CHO cell damage in a rotary positive displacement pump", Biotechnology Progress, 2010, pp. 1-7, Jun. 29, 2010.

* cited by examiner

*Primary Examiner* — Jon P Weber
*Assistant Examiner* — Teresa E Knight
(74) *Attorney, Agent, or Firm* — Nixon & Vanderhye P.C.

(57) ABSTRACT

This invention relates to cell-independent processes which mimic cellular bioremodelling and produce organized biomaterials which have mechanical properties and viable cell densities suitable for use as functional tissue implants. The biomaterials are produced by providing a gel comprising a matrix of scaffold fibers of and an interstitial fluid; and plastically compacting the gel to produce the biomaterial. The biomaterials may comprise 3D structures such as layering, alignment and meso-scale zonal heterogeneities of cells and matrix which mimic native tissue structure. Biomaterials with biomimetic structure as described herein may be useful in a range of therapeutic applications.

39 Claims, 24 Drawing Sheets

CELL-INDEPENDENT FABRICATION OF TISSUE EQUIVALENTS

This application is the US national phase of international application PCT/GB2005/002631, filed 5 Jul. 2005, which designated the U.S. and claims priority of GB 0415080.1, filed 5 Jul. 2004, the entire contents of each of which are hereby incorporated by reference.

This invention relates to methods for preparing tissue equivalent implants for the repair and/or replacement of damaged tissue in an individual and implants produced by such methods.

Conventionally, tissue-engineering aims to convert an initial cell-scaffold construct into a tissue-like architecture which has biomimetic function. This conversion process generally involves cell-based remodelling in culture. However, in most cases, cell-based remodelling has proved slow (often taking weeks), difficult to control and costly with only limited ability to organise bioartificial materials or 'tissues' (M. Eastwood et al, *Cel. Motil. Cytoskel.* 1998 40 13; D. Huang, et al *Ann. Biomed. Eng.* 1993 21 289). This is partly attributable to limitations of perfusion/hypoxia which are related to tissue density (e.g. in ligament, dermis and muscle). It is compounded by a limited understanding of how cells actually produce particular native micro-structures (i.e. 3D cell-matrix organisation). The material composition and, more particularly, the 3D nano-micro (meso) scale structure of bioartificial, engineered constructs are critical to their success (R. A. Brown, in *Future Strategies for Tissue and Organ Replacement* (Eds: J. M. Polak, L. L. Hench, P. Kemp), World Scientific Publishing, Singapore (2002) 48; R. A. Brown et al *Wound Rep. Reg.* (1997) 5 212).

Native matrix scaffolds (e.g. collagen, fibrin, hyaluronan, fibronectin) have been used produced with appropriate biomimetic 3D meso-scale structure for cell/tissue growth. However, our limited ability to control assembly of biomimetic structures at this scale, particularly using native proteins and living cells has restricted progress. This is partly due to limited knowledge of natural protein polymer 3D assembly (F. Volrath, D. P. Knight, *Nature* 2001, 410, 541), making it necessary to rely on cells to carry out the necessary assembly/ remodelling process.

The cell-seeded collagen gel is an excellent biomimetic starting point, but is mechanically very weak (Z. Feng et al *Artificial Organs* 2003, 27, 84; L. Krishnan et al *Tissue Eng.* 2004 10 241) and slow to become stronger in culture.

Examples of conventional cell-based fabrication have used a number of systems. At their simplest, these use no support scaffold at all, being a development of a superconfluent 2D culture (S. Calve et al *Tissue. Eng.* 2004, 10, 755). Huang et al (Huang et al 1993 supra) produced ligament-like tissues using collagen gels under uniaxial endogenous tension, reaching break stresses of 0.14 MPa, after 12 weeks. Feng et al (Feng et al 2003 supra) found that non-loaded, non-orientated collagen gels reduced in diameter by 85% over 10 weeks in culture, with a yield stress of around 0.1 MPa. Garvin et al (Garvin, J. et al *Tissue Eng.* 2003, 9, 967) reported the use of loading to give cell/fibril alignment and the generation of an epitenon-like surface layer. Break stress of 7-day constructs rose from 0.11 to 0.33 MPa (modulus 1.8 MPa) with 1 h/day, 1% strain, 1 Hz cyclical loading.

Insoluble collagen sponges (I. V. Yannas et al *Science* (1982) 215, 174) (e.g. Integra™) have greater strength than collagen gels. Collagen sponges are random porous structures derived from extensively pre-polymerised fibres, sheets or meshes and are often produced from reconstituted or fragmented shredded insoluble polymer (e.g. animal collagens from skin, tendon, etc) by thermal compression at high temperatures (i.e. well above normal protein denaturation temperatures; for example >60° C.). The micro-architecture of collagen sponges is therefore neither biomimetic nor easily remodeled by cells. Techniques for strengthening insoluble collagen sponges with high temperature and compression, for drug delivery have recently been described (Z. Rusczcak, W. Friess, *Adv. Drug Delivery Rev.* 2003 55 1679; US 2003095997; US 2003133967)

Other practical alternatives include 'small intestinal submucosa' (SIS) collagen membrane (S. F. Badylak et al. *J. Biomed. Mater. Res.* 1995 29 977). Though SIS has excellent mechanical and cell growth properties, it remains a harvested, processed animal product. As such, it is acellular and its collagen architecture and 3D organisation is predetermined by the animal tissue.

The present invention relates to the surprising finding that physical processes that require little or no cell participation (i.e. cell independent processes) can effectively mimic cellular bioremodelling and produce organised scaffold-cell matrices which have mechanical properties and viable cell densities suitable for use as functional tissue implants. 3D tissue-like structures such as layering, alignment and meso scale zonal heterogeneities of cells and matrix can also be formed, mimicking the structure of native tissues, such as tendon, nerve and skin. Nano-micro scale, cell-independent fabrication of tissue templates with biomimetic structure as described herein may be useful in a range of therapeutic applications.

An aspect of the invention provides a method of producing a biomaterial comprising:

providing a gel comprising a matrix of scaffold fibres and an interstitial liquid; and, plastically compacting the gel to produce said biomaterial.

Plastic compaction may, for example, increase the density and mechanical strength of the scaffold matrix. A biomaterial produced by the present methods may be useful, for example, in the production of a tissue equivalent implant.

A tissue equivalent implant is a device for implantation into an individual to repair or replace endogenous tissue, which, for example, may be damaged or diseased. Examples of diseased tissues which may be repaired or replaced by tissue equivalent implants include nerve, tendons, cartilage, skin, bone, urogenital elements, liver, cardiopulmonary tissues, kidney, ocular tissues, blood vessels, intestine, and glands.

Preferably, a tissue equivalent implant is a structural biomimetic of the host tissue, and in particular mimics its structure at the cellular level (i.e. nano-micro meso) scale). A tissue equivalent implant may contain cells distributed as in the native tissues at the meso-scale in appropriate layers, zones, depots and channels.

The structure and distribution of cells in different tissues is well known in the art. Examples of meso-scale layers may include epithelial (keratinocyte) and stromal (dermal fibroblasts) layers in skin; entry-, connecting- and exit-ramp zones in a nerve regeneration conduit: endothelial (lining), smooth muscle contractile stroma (two or more) and outer adventitia layers in blood vessels. Examples of channels in an implant might include tracks for invasion of capillaries of nerves post-implantation. Examples of zones might include a depot of hormone secreting cells held in a construct close to a perfusing capillary bed.

In general, suitable scaffold materials may include any spontaneously aggregating or fibril-forming hydrogel in which the fibres do not have strong ionic surface charge at physiological pH. The fibres of the scaffold material are preferably not cross-linked or substantially polymerised. Preferred scaffold materials have low hydration/swelling properties to facilitate plastic compaction. Many suitable fibril-forming scaffold materials are known in the art. A fibril forming material is a material comprising soluble monomer molecules that can be made to self-associate by packing to form discrete (insoluble) fibrils and fibres.

Suitable scaffold fibres include naturally occurring polymers, for example proteins, such as silk, fibrin, fibronectin, elastin or collagen (e.g. collagen type I), glycoproteins such as fibronectin, or polysaccharides such as chitin, or cellulose. In some preferred embodiments, the scaffold fibres are made collagen. Native fibril forming collagen types are preferred including collagen types are I, II, III, V, VI, IX and XI and combinations of these (e.g. I, III V or II, IX, XI). For example, collagen type I may be used as the scaffold material.

In other embodiments, the scaffold may be a synthetic polymer i.e. a polymer that is not naturally present in the human or animal body. Suitable polymers include organic polymers such as polylactone, polyglycone and polycaprolactone and inorganic polymers such as phosphate glass. A synthetic polymer may be adapted to reduce inherent swelling potential at the chosen pH (usually around neutral). Swelling is usually caused by surface charge and osmotic pressure. In such cases, the surface chemistry of the polymer may be modified to ensure appropriate hydrophilic properties without significant fixed charge density.

The scaffold may be a composite material comprising two or more different types of fibre. For example, the scaffold may comprise fibronectin and collagen, collagen and polylactide, fibrin and collagen, soluble glass fibres and collagen or fibrin, or fibrin, collagen and fibronectin A gel as described herein is formed by the coalescence and elongation of fibrils of the scaffold material, as the fibrils form a continuous network around the aqueous interstitial liquid which originally held the monomers. For example, triple helical collagen monomers may be initially dissolved in dilute acid and then induced to polymerise (aggregate) to fibrils (e.g. at 37° and neutral pH). As the fibrils polymerise, there is a phase change and the solid network of fibrils 'supports' the remaining interstitial liquid in approximately the same volume and shape—i.e. it gels.

Phase transition from soluble monomer to solid polymer is characteristic of a gel and is important in providing the properties described herein. Gels are distinct from 'sponges', which may be formed from pre-polymerised fibres.

Unconfined compaction of a gel expels the interstitial liquid and it does not return on removal of the load: i.e. the gel undergoes a plastic compaction. The scaffold matrix in the untreated gel is generally in a gross, hydrated form. Plastic compaction of the gel collapses the scaffold structure without loss of structural detail, dehydrating the scaffold in the gel, and leading to increased density and strength.

The interstitial liquid is typically an aqueous liquid, although other organic solvents may be used in certain abiotic applications. For example, the liquid may be water with solutes such as salts and proteins dissolved therein. In some embodiments, the interstitial liquid is a cell culture medium suitable for the growth and proliferation of cells.

Preferably the gel is seeded with cells, in particular human or other mammalian cells. These cells remain viable when the gel is compacted into the biomaterial.

The gel may comprise cells that confer tissue functionality and provide structures which replace or facilitate the repair of endogenous tissue. For example, the gel may comprise one or more of muscle cells to provide contractile structures, vascular and/or neural cells to provide conductive elements, metabolically active secretory cells, such as liver cells, hormone synthesising cells, sebaceous cells, pancreatic islet cells or adrenal cortex cells to provide secretory structures, stem cells, such as bone marrow-derived or embryonic stem cells, dermal fibroblasts, skin keratinocytes, (and combination layers of the two), Schwann cells for nerve implants, smooth muscle cells and endothelial cells for vessel structures, urothelial and smooth muscle cells for bladder/urethra structures and osteocytes, chondrocytes, and tendon cells for bone and tendon structures. In some embodiments, the cells seeded into the gel may include fibroblasts.

Cells may be distributed interstitially within the gel in any arrangement. For example, the cells may be distributed homogeneously throughout the gel or distributed in defined zones, regions or layers within the gel.

The cells are preferably seeded into the gel before compaction, for example when the gel is cast. Cells may be seeded within the matrix by mixing them with the liquid scaffold matrix and then allowing the liquid matrix to solidify into a gel. Seeding of the matrix is preferably performed under suitable conditions of temperature, pH, ionic strength and sheer to maintain viability, prior to gel formation.

Optionally, when cell attachment to the scaffold is required, the cells may be incubated in said gel for 24 hours or less, 12 hours or less, 6 hours or less, 3 hours or less, or 1 hour or less, most preferably 0 to 2 hours before compaction.

The reduction in gel volume caused by compaction will be inversely related to the increase in cell density within the gel. Thus, compaction of the gel as described herein may increase the cell density by 5 to 200 fold, more preferably 10 to 100 fold.

The initial cell density in the gel may be from about $1 \times 10^4$ to $1 \times 10^7$ cells per ml, more preferably from about $5 \times 10^5$ to $1 \times 10^6$ cells per ml. The cell density after compaction may be from $1 \times 10^7$ to $1 \times 10^9$ cells per ml, more preferably from $5 \times 10^7$ to $5 \times 10^9$ cells per ml.

The final cell density in the compacted gel may be varied, depending on the intended application of the compacted gel, by altering the initial cell density and/or the amount of compaction. For example, for tissue constructs needing high cell densities (such as liver, kidney or gland constructs), the amount of cells seeded into a gel and/or the amount of compaction may be increased. Final cell density may be further increased by secondary compaction as described herein.

The proportion of cells in the compacted biomaterial will depend partly on cell size. Small cells, such as red blood cells, may represent a lower proportion of the compacted biomaterial relative to larger cells, such as fibroblasts, even when present at the same cell densities. In general, cells may represent at least 1% v/v, at least 5% v/v or at least 10% v/v of the compacted biomaterial. For optimal physical properties, a biomaterial construct may comprise less than 50% v/v, less than 40% v/v or less than 30% v/v cells.

The properties of a biomaterial or implant may be adjusted for a particular usage or application by varying the ratios of individual constituents (e.g. in % v/v) in the biomaterial. For example, the proportion of matrix component may be altered to change the strength of a biomaterial, the proportion of cells may be altered to change the cell activity of a biomaterial and/or the proportion of microchannelling may be altered to change the perfusion properties of the biomaterial.

The plastic compaction process may be optimised to achieve the desired final ratio of collagen, cells and channel forming inserts from a standard starting gel. A standard gel, for example, may comprise 1-4% collagen, $0.2-10 \times 10^6$ cells per ml and 0.2 to 2% channeling fibres or granules.

Cells in the compacted biomaterial are susceptible to desiccation. To reduce cell death and/or damage associated with desiccation, the gel may be compacted in an aqueous liquid, for example a culture medium, such as DMEM, Ham's or Eagle's medium or a physiological buffer such as Ringer's or PBS. For non-cellular biomaterials, any solvent compatible with the scaffold matrix may be used.

Cells are also susceptible to hypoxic cell death and/or damage due to the high cell densities within the compacted biomaterial. To reduce and/or prevent cell death or damage, an implant or biomaterial may be stored under conditions which maintain viability but which do not support cell growth, until ready for use. For example, the implant or biomaterial may be stored at low temperature, such as 0 to 5° C., preferably 4° C.

Plastic compaction as described herein means deforming an object such as a gel to reduce its volume, such that the object substantially retains its new volume, even after the cause of compaction is removed. Plastic compaction is a rapid, cell-independent process which results from subjecting the gel to a physical treatment, such as an external force or pressure, which expels interstitial liquid from the gel. Plastic compaction is distinct from the slow process of cell-driven contraction, which occurs through the intrinsic action of cells growing within the gel i.e. plastic compaction is not cell-mediated and does not occur through the action of cells which are cultured within the gel.

Cell-mediated contraction is only capable of producing a small fraction of the compaction caused by plastic compaction as described herein. Furthermore, cellular contraction occurs with random vectors so the overall contracting vector is an average for the whole cell population. Plastic compaction employs has a vector in one, two or more defined directions and the direction, rate and extent of the compaction is controllable.

Plastic compaction allows the cell content, matrix density and fluid content of the biomaterial to be precisely defined. Furthermore, local enhancement of one or more of these parameters within the biomaterial is possible and the spatial position and pattern of these local enhancements is controllable, for example to produce layering, zoning or channeling.

In some embodiments, an object subjected to plastic compaction does not have any substantial swelling tendency, which might subsequently reverse the compaction without further cell culture or processing steps.

In other embodiments, a tissue equivalent implant may undergo some re-swelling during use. For example, although a compacted collagen matrix containing chondrocytes does not re-swell initially, the growing chondrocytes synthesise proteoglycans/GAG which take up liquid and swell the implant. The swollen implant structure may be particularly useful in mimicking the structure of cartilage.

The amount or extent of compaction may be varied, depending on the application of the biomaterial. Compaction of the gel, for example by compression, may result in a reduction in one or more dimensions of the gel of at least 5 fold, at least 10 fold or at least 20 fold. The one or more dimensions may be reduced by 200 fold or less, 150 fold or less, or 100 fold or less. In preferred embodiments, the thickness of the gel is reduced by compaction.

For example, the volume of the gel may be reduced by 50% or more, 60% or more, 70% or more, 80% or more, 90% or more, 95% or more, 99% or more, or 99.9% or more by plastic compaction The time required for compaction will be less than the time required for cell-driven contraction to occur and will vary in accordance with the compaction method and the conditions used. For example, compaction may occur in less than 12 hours, less than 6 hours, less than 3 hours, less than 1 hour, less than 30 minutes or less than 10 minutes. In some preferred embodiments, the gel may be compacted in 2 minutes or less, or 1 minute or less.

Plastic compaction of the gel may be associated with the loss or removal of some or all of the interstitial fluid from said gel For example, the amount of fluid lost or removed from the gel by plastic compaction may be at least 50%, at least 60%, at least 70%, at least 80%, at least 90%, at least 99%, or at least 99.9% of the original fluid content of the gel.

Preferably, some interstitial fluid remains after compaction, for example at least 10%, at least 1% or at least 0.1% of the original fluid content of the gel. In preferred embodiments, the gel is not subjected to drying or desiccation, for example heat-, freeze-, airflow or vacuum drying, following plastic compaction, as dehydration kills cells and damages biomaterial structure.

The extent of compaction may depend upon the surface charge and hydration equilibrium of the scaffold material. Compaction beyond the hydration equilibrium may cause a compacted scaffold, placed into aqueous environment, to partially re-swell (i.e. the compaction is partly non-plastic).

Plastic compaction may expel interstitial liquid from the gel or draw interstitial liquid out of the gel. More than one method may be used to compact the gel, either sequentially or simultaneously. In some preferred embodiments, compaction occurs with one or more defined vectors and the interstitial liquid is expelled from the gel through one or more defined fluid-leaving surface. The number and arrangement of vectors of compaction and fluid-leaving surfaces may be selected in order to produce defined structures, such as lamellae, within the biomaterial, as described herein.

Interstitial liquid may be expelled by applying a mechanical force to the gel, for example positive or negative pressure.

A mechanical force may include a compressive force.

The amount of compressive force applied to the gel to achieve the desired compaction depends on the particular circumstances and may be readily determined by the skilled person. For example, a suitable compressive force may be 0.1 to 10 N, e.g. 1 N. Preferably the gel is unconfined when subjected to the compressive force.

Any suitable method of applying a compressive force to the gel may be employed.

For example, a gel may be compressed by one or more of: applying a static load (for example a dead weight) to the gel, applying a load through a hydraulic or cam or passing the gel through rollers.

In some embodiments, a gel may be compressed by extrusion through the gel a constricting orifice. A constricting orifice, for example may comprise a conical chamber which compresses the gel as it passes through. The conical chamber may comprise porous walls to allow egress of interstitial fluid from the gel to facilitate compaction.

In some embodiments, compressive force is applied by expanding a balloon within said gel to compress the gel against a solid surface. The solid surface may for example form a tube around the gel, allowing the formation of tubular implant constructs.

In some embodiments, compressive force is applied by centrifugation. Centrifugation of a standard hydrated gel at the base of a dry centrifuge tube reduces the fluid content of the construct by plastic compression—expelling interstitial liquid into either a dry porous support or to a collecting chamber. The amount of fluid loss may be regulated by the speed and duration of centrifugation.

Methods of compression where the gel remains stationary (e.g. a dead weight applied to gel or a hydraulic or cam applied load) are known as "static" methods of compression. Methods where the gel is moved during compression are known as "dynamic" methods of compression (e.g. passing the gel through rollers or extruding the gel through a constricting orifice).

Alternatively and/or additionally, interstitial liquid may be drawn from the gel to cause compaction. Any suitable method of removing liquid may be employed. For example, liquid may be removed by one or more of draining, evaporation, suction, capillary pressure, osmosis or electro-osmosis.

Liquid may be removed by capillary pressure by 'blotting' the gel on an absorbent material. The absorbent material may be paper, in particular blotting paper. The material may be removed from the gel after compaction. For example, a hydrated gel (e.g. a collagen gel) may be compacted by blotting through a supporting wide weave (>100 micron) nylon mesh into a sheet of porous filter paper to reduce the mass of the material to a fraction of its original dimensions with concurrent increase in density. The rate of compaction is slower than for methods which include mechanical compression. However, the rate of compaction may be increased by the addition of a second mesh and blotting layer on the upper surface of the gel.

Liquid may be removed by evaporation, for example by incubating the gel under conditions that promote evaporation, for example, at lower than atmospheric pressure and/or at temperature higher than room temperature. This is generally less preferred when the gel contains cells, as evaporation removes water but not solutes so the osmolarity of the gel will increase as it compacts to form the biomaterial.

Liquid may be removed from the gel by suction. For example, the application of a vacuum (e.g. a mechanical pump in a multi well plate system) to a standard hydrated collagen gel which is resting on a 0.45 micron filtration membrane results in a reduction in fluid content over a few minutes, depending on the dimensions and type of construct and level of vacuum.

In some embodiments, liquid may be conveniently drained by tilting the gel. Liquid then drains from the gel under the mechanical effect of gravity and gradient. For example, drainage of a standard hydrated collagen gel under its own weight in an angled orientation in a humid chamber at room temperature, will give suitable liquid loss and therefore compaction over 3 hours and an exponential loss of fluid with a 6-fold reduction in gel mass over 3 days.

Certain methods of plastic compaction, such as osmosis, electro-osmosis, or evaporation methods, specifically remove solvent from the gel but not solute. This may alter the ionic properties (e.g. salt concentration, pH) of the fluid in the gel.

When cells are seeded within the scaffold of the gel, the gel environment is preferably maintained at physiological conditions (e.g. temperature, pH, hydration and ionic strength) for the cells to survive. In such biotic embodiments, it is preferred that plastic compaction does not alter the ionic properties of the gel fluid significantly from physiological conditions.

In abiotic embodiments, when the gel does not contain cells, the gel environment need not be physiological and any method of plastic compaction is suitable, including those that alter the ionic properties of the gel fluid, such as osmotic methods.

Two or more different compaction methods may be used to compact the gel, either sequentially or simultaneously.

For example, the gel may be plastically compacted by mechanical compression and, preferably simultaneously, liquid may be extracted from the gel by one or more of: suction, capillary pressure, osmosis, electro-osmosis. In some embodiments, a combination of capillary pressure and mechanical compression may be employed for rapid compaction.

A method as described herein may include more than one, for example 2, 3, 4 or more distinct phases of plastic compaction.

As described above, interstitial liquid may exit the gel though a defined fluid leaving surface of the gel. In some embodiments, during plastic compression, for example of a collagen gel, the outer 'skin' of the gel (fluid leaving surface) may act as a filter, allowing out fluid and solutes but retaining collagen fibrils, cells and/or other macromolecular aggregates, such as particle inclusions, growth factor depots/vesicles and mineralized particles (e.g. bone mineral or ceramic biomimetic particles) at the gel surface. Additionally or alternatively, the gel may be supported on a porous sheet or membrane which assists filtration of the liquid being removed from the gel. This may lead to some regional heterogeneity of compaction at the gel surfaces, particularly where there is a specific fluid 'exit' surface. A dense layer of cells, collagen or other macromolecular aggregates may thus be localized at a gel surface. This lamellae structure may be useful in the production of tissue equivalent implants. The scale of this fabrication technique may be geared, for example, to produce architectural features or structure on a nano- or micro-level.

The properties of the scaffold matrix are important in determining how the repair or regeneration of tissue is organised by cells and the initial scaffold structure effectively dictates most of the later downstream 3D structure. For many applications, it is therefore useful for the cells and fibres in a tissue equivalent implant to be aligned.

Cells and/or fibres of the scaffold matrix may be aligned, for example by applying tension across the gel. Tension may be applied before, during and/or after plastic compaction.

The tension is preferably uniaxial and the gel may be subjected to 5-50% uniaxial strain, preferably 10-30% uniaxial strain. The fibres and, if present, seeded cells, align in a parallel orientation to the direction of principle strain.

For example for a collagen gel, a strain of 5 to 30%, preferably 20-25%, may be employed.

A method as described herein may comprise applying tension to the gel to align said scaffold material fibres and/or said cells.

The gel may, for example, be placed under uniaxial tensile load et the start of the plastic compaction process, or part way through (e.g. 20 to 60% compression), and then returned to the plastic compaction regime, such that the fibril alignment induced by the tensile strain is fixed into the gel, giving an aligned dense composite, which, in some embodiments, may contain living cells.

Alternatively, fibres may be aligned by clamping the ends of the gel and applying a uniaxial strain across its long axis before the gel is plastically compacted.

The alignment of cells and fibres within a scaffold matrix is described in Eastwood et al (1998).

In addition to the scaffold, cells and interstitial liquid, the gel may include further components. In particular, the gel may comprise solid elements, for example capillary filaments or porous beads Capillary filaments may be insoluble or soluble fibres of a rigid, solid polymer. Suitable filaments are preferably less than about 100 μm in diameter.

Soluble filaments inserted within the gel may dissolve to form capillary channels within the gel. These capillary channels within the gel may be useful for example, for one or more of: perfusion, drug and/or gene and/or media delivery into the scaffold; and anastomosis with a recipient's circulation.

Suitable soluble filaments may be made from soluble phosphate glass, polycapryolacetone, polyacetate, polyglycolic acid, silks, polysaccharides, or fused or crystallised salts.

Insoluble filaments may be useful for delivering optical therapies, optical monitoring, signal transmission and/or strain detection. Suitable insoluble filaments may be made from glass.

Capillary filaments may be inserted between the layers of a gel, added to the gel before casting or may be inserted into the gel after casting. In embodiments comprising more than one cast gel, the filaments may, for example, be sandwiched between the gels.

In some embodiments, the gel may comprise porous beads. Plastic compaction of the gel matrix forces fibres of the scaffold into pores of the porous beads to provide a tightly bonded structure. This may be useful, for example, when seeded with osteoblasts or chondrocytes, as artificial bone or calcified cartilage substitute tissues.

Suitable porous beads may be approximately 100-500 microns in diameter and may be of any solid material, for example porous ceramic, glass, phosphate glass, hydroxyapatite, or bone mineral preparations (from native bone removal of organic phase).

The ratio of granules:gel:cells will depend on the particle size and the tissue properties required (e.g. dense or loose packed hard tissue).

In some embodiments, a linear construct (e.g. a rod, strap or roll construct) may contain porous beads as described herein at the ends, to facilitate attachment of the construct in vivo, for example by screwing directly into bone.

Multi-layered biomaterials are useful because native tissues are layered at the micron level and these layers may play a role in the organisation of cellular tissue construction and the segregation of cell function.

The methods described herein allow the production of micro-structured biomaterials, for example biomaterials with multiple (i.e. two or more) layers. These biomaterials may be particularly useful in the production of tissue equivalent implants.

Layers also facilitate movement of tissues (gliding bending complaint layers), help with perfusion through and between layers, permit rapid anisotropic nutrient movement along and between layers e.g. in tendon, and direct in-growth of capillaries, nerves, stroma etc. after implantation (in-growth in the plane or channel of least resistance).

A method of producing a biomaterial may comprise:
overlaying a first and a second gel, wherein each gel comprises a matrix of scaffold fibres and an interstitial fluid; and,
plastically compacting the gels to produce a biomaterial, said first and second gels forming layers in said biomaterial.

In some embodiments, the first and the second gel may be different regions of the same gel, which are brought into contact, for example by folding or rolling the gel.

In other embodiments, the first gel and the second gel may be different gels i.e. two or more gels may be overlaid.

The two or more gels may have different functions and/or activities and may differ in one or more physical characteristics. For example, the gels may differ in one or more of: organisation of fibres in the scaffold, type of fibres, density of the scaffold, and the concentration, type or mixture of macromolecular aggregates, porous particles, and/or biological depots (e.g. for growth factors, hormones, enzymes and/or minor matrix proteins) which are present within the gels.

The gels may be plastically compacted to form a single sheet of biomaterial having two or more layers.

Preferably, the gels are sufficiently fused so as not to separate easily under mechanical load, for example the interfaces may be stable to 1 to 10% of the break strain of the layers themselves, more preferably 5-10%.

The merging of two or more gels allows complex tissues and organs to be built up layer by layer. This may be useful, for example, in the production of implants for the repair or replacement of nerve, tendons, cartilage, skin, bone, urogenital elements, liver, cardiopulmonary tissues, kidney, ocular tissues, blood vessels, intestine, and glands.

Implants for the repair of nerve tissue (PNS or CNS), for example, may be produced with an outer sheath of collagen and cells around a core of neural guiding material (e.g. fibronectin). Cell/growth factor (e.g. NGF) depots may be positioned at the entrance and exit ports.

Implants for the repair of ligament, for example, may be produced by incorporating hydroxyappertite beads or granules into the ends of a PC collagen rod to form a ligament implant with hard bony attachments at each end for fixing in position.

Implants for the repair of cartilage may be produced, for example, by producing a roll or spiral construct of collagen seeded with articular chondrocytes (for example), applying secondary compression to the roll (perpendicular to the long axis) and culturing in standard growth medium for about 7 days. Resident chondrocytes will re-swell the construct (by synthesis and water uptake of proteoglycans) to form a cartilage implant.

Connective (or other) tissue implants may be produced with predetermined vascular channels by forming a spiral (or layered) construct as above with collagen, but interplacing parallel fibres (ideally 20 to 200 microns in diameter) between the layers, made from a rapidly soluble phosphate glass. When the glass fibres dissolve in an aqueous medium (e.g. after implantation or in a bioreactor), they leave channels through the collagen implant which act as guidance tracks for capillary (nerve) ingrowth. Such structures follow and fill these channels, as the paths of least resistance.

Methods described herein may be conveniently performed using a mechano-bioreactor adapted to apply suitable mechanical loads (e.g. vectored compression and tension, preferably as part of a pre-programmed sequence) to a gel, for example as part of an integrated, automated culture process. The mechano-bioreactor is preferably adapted to enable culturing and/or incubation of a three-dimensional tissue equivalent implant and may, for example, comprise uniaxial tensing means (conferring for example, cyclic or ramp load tension on a construct) and optical and electrochemical (oz plus glucose) sensors.

Alternatively, a tissue equivalent implant (cellular or abiotic) may be made using a continuous flow-through process (of the "conveyor belt" type) with a sequence of steps, including the plastic compaction step.

An aspect of the invention provides a method of producing a tissue equivalent implant from biomaterial produced as described above. For example, a method of producing a tissue equivalent implant may comprise either;
  a) plastically compacting a gel comprising a matrix of scaffold fibres and interstitial fluid to produce a biomaterial, or,
  b) overlaying two or more gels, wherein each gel comprises a matrix of scaffold fibres and interstitial liquid; and plastically compacting the gels to produce a biomaterial having two or more layers;
and,
producing said implant from said biomaterial.

Each gel may further comprise viable cells, as described above.

Plastic compaction may be carried out as previously described. In some preferred embodiments, the gel may be subjected to mechanical compression.

Tension may be introduced across the gel to align the cells and scaffold fibres. Tension may be applied before, during or after plastic compaction of the gel.

As described above, methods of the invention may be performed at lower than room temperature, for example at about 4° C. so that seeded cells remain viable despite increases in perfusion distances as cell density increases. Further gel layers may be added as described herein.

Cell density and mechanical properties of the implant are determined by the conditions of the plastic compaction.

The biomaterial may for example be moulded and/or shaped to produce said implant. The gel may be moulded into a predetermined shape, for example during casting and/or plastic compaction. In some embodiments, the shape may be further moulded following the plastic compaction step and/or subjected to further compaction.

The tissue equivalent implant may be shaped or moulded into any convenient implant form, for example, a patch, tube, tape, strip, ring, roll, sheet or thread. The final shape of the tissue equivalent implant will depend on the particular context in which it is to be used.

The tissue equivalent implant may be moulded to a pliable form suitable for further shaping. Plastic compaction, for example, may be symmetrical or asymmetrical.

Following plastic compaction and production of the implant construct, the construct may be implanted immediately into an individual or subjected to further incubation to modulate subtle properties of the scaffold matrix such as stiffness, elastic modulus etc.

In embodiments in which a sheet of biomaterial is produced by plastic compaction, the biomaterial sheet may be rolled up to form a roll of biomaterial.

This allows the rapid assembly of 3 dimensional implants, which may for example be conveniently handled by a surgeon, from one or more flat 2 dimensional layers of biomaterial.

In other embodiments in which a sheet of biomaterial is produced by plastic compaction, the biomaterial may be folded to produce a construct comprising two or more layers. This construct may be further cut or shaped as required.

Constructs may be rolled or folded around a central fibre/needle to produce an implant with a central channel.

Soluble fibres (e.g. phosphate glass) may be positioned between layers of the construct. These fibres subsequently dissolve to leave channels for neovascularisation or re-innervation in vivo.

Constructs may be rolled or folded around sensing/monitoring fibres (e.g. 100-200 micron optical fibre for $O_2$ monitoring) to give continuous real time measure of cell matrix structure status e.g. post implantation or in bioreactor.

The rolled or folded multi-layered biomaterial may be used directly as a tissue equivalent implant or may be plastically compacted further, for example, to adhere the layers together, achieve the desired dimensions, increase cell density or to improve other properties.

Secondary compaction dramatically improves the properties of the biomaterial. For example, once formed, the multi-layered construct comprising viable cells may subjected to a second compaction to expel more interstitial liquid and provide greater strength. Secondary compression of a roll construct typically removes 60% of the remaining liquid and produces a dense strap of strong material—break stress may be increased by up to 3-fold or more (0.6 mega pascals to 2 mega pascals). Secondary compression or compaction may be carried out using the techniques described above.

A rolled or folded construct may be stored under conditions which maintain cell viability but which reduce or prevent cell growth. For example, the roll may be stored at 0 to 5° C. This prevents cell death or damage related to high cell densities, for example hypoxic cell damage.

If the biomaterial has one or more layers or regions, the layers or regions may be arranged to provide a complex roll or spiral assembly made up of separate zones or regions, which may be useful for specific implant applications. For example, the layers may be concentric, with an outer layer and one or more inner layers. In addition, rolling up the sheet in different directions can provide different construct geometries.

For example, a roll implant construct for use in the repair and/or replacement of nerve tissue comprising four distinct regions is shown in FIG. 23. The construct is assembled by overlaying an outer sheet 1, a nerve entry substrate 2, a long range fibre guidance material 3 and a nerve exit material containing growth factors 4, compacting the layers and then rolling them up to form the final spiral assembly.

A folded or rolled biomaterial may be used as a tissue equivalent implant i.e. it may be introduced into a human or animal body for the repair or replacement of endogenous tissue.

Another aspect of the invention provides a method of treatment of a damaged tissue in an individual comprising;
producing a tissue equivalent implant using a method described herein and,
fixing said implant to said damaged tissue to repair and/or replace said tissue.

The implant may be fixed by any convenient technique. For example, it may be sutured or glued in place.

All of the constructs described herein e.g. rolled, folded, secondary compacted biomaterials, will take sutures and can be sutured surgically into body sites even when under muscle load.

Another aspect of the invention provides a biomaterial or tissue equivalent implant produced by a method described herein.

Aspects of the present invention will now be illustrated with reference to accompanying figures and the experimental exemplification below, by way of example and not limitation. Further aspects and embodiments will be apparent to those of ordinary skill in the art.

All documents mentioned in this specification are hereby incorporated herein by reference.

Figure 1:
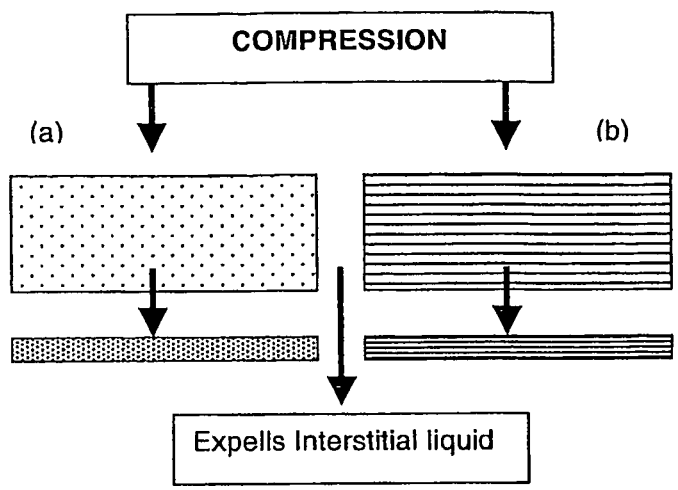
FIG. 1 shows plastic compaction of (a) an isotropic gel and (b) an anisotropic gel by mechanical compression.

Table 1 shows collagen construct mean thickness (single layer) at 3 stages of compression.

Table 2 shows cell viability at stages during the compression process, from the starting cell preparation and freshly cast gel (pre-compression) to post-compression, with applied tension or desiccation.

Methods

Formation of Cellular and Acellular Collagen Gels

Acellular collagen gels were made, as described previously [1,21] by neutralising 2.4 mL of sterile rat tail type I collagen (2.16 mg·mL$^{-1}$ protein in 0.6% acetic acid: First Link (UK) Ltd, West Midlands, UK), 0.3 mL of 10× concentration Eagle minimum essential medium (EMEM) (Gibco Chemicals, Invitrogen, Scotland, UK) and 0.3 mL of Earle's balanced salt solution (EBSS), (Sigma-Aldrich Co., Dorset, UK) with 5 M sodium hydroxide (Merck, Leicestershire, UK). For cell-seeded gels, 106 human dermal fibroblasts suspended in 0.3 mL of Dulbecco's modified Eagle's medium (DMEM) with 10% foetal calf serum (FCS), were mixed with the collagen solution immediately after neutralisation, in place of the EBSS. Cell density at the point of casting was 0.33×10$^6$ ml$^{-1}$ collagen gel. Gels were cast into rectangular moulds (33× 13×4 mm) and set/stabilised in a 37° C., $CO_2$ incubator for 70 min for acellular gels (experimental range 35 to 180 min) and between 1 and 3 hours for cellular gels to allow cell attachment. Determinations of fluid-loss from collagen gels (self-compression) were based on % fall in wet-mass. Transfer of gels from casting chamber for initial wet-mass used a customised flat scoop spatula for minimal handling with subsequent incubations in a sealed humid chamber (room temperature) and re-weighing after 0.5, 1, 2, 3, 4, 24, 48, 120 hours (either horizontally or inclined at 45°: n=3 for each determination). Almost all of the change in wet-mass occurred in the first 3 hours and so the horizontal 3 hours 'self-compression' gels were used as stable controls (giving 57% compaction).

Cell Culture and Cell Viability Assay

Normal human dermal fibroblasts were prepared by routine explant culture of stripped and defatted human dermis (obtained freshly from operating theatre, with full ethical approval, following surgery for breast reduction or abdominoplasty), described previously[21,22] Fibroblasts growing out of 2-4 mm adherent tissue fragments were expanded in Dulbecco's modified Eagle's medium (DMEM: Gibco, Paisley, Scotland) containing 10% FCS (First Link (UK) Ltd.) and streptomycin/penicillin (500 µg/ml and 500 units/ml respectively: ICN Biochemicals, Thyne, UK.) under 5% $CO_2$, 37° C. Cell viability determinations were made, at each stage of plastic compaction, by incubating constructs for 1 hour in DMEM+10% FCS containing 1 µM calcein AM (to locate living cells) and 1 μM ethidium homodimer (staining dead cells). Live and dead cells appeared green and red, respectively, by fluorescence microscopy and the live:dead ratio was estimated by cell counting form micrographs through a grid (total of 4000 cells counted from randomised areas).

Plastic Compression and Tension Pre-Alignment

Following setting and incubation, gels were routinely compacted by a combination of compression and blotting using layers of mesh and paper sheets as shown in FIG. 1. Briefly, 165-μm thick stainless steel mesh (mesh size ~300 μm) and a layer of nylon mesh (~50 μm mesh size) were placed on a double layer of absorbent paper with the two stainless steel spacers (300 μm thick, FIG. 1a). The collagen gel was placed (between the spacers) on the nylon mesh, covered with a second nylon mesh, and loaded with a 50 g flat plastic block (Delrin polymer) for 5 minutes at room temperature, giving a flat collagen sheet (20-40 μm thick) protected between 2 nylon meshes. Characterisation of plastic compression alone (i.e. without enhanced blotting) was without the absorbent paper.

Blotting inevitably made some contribution to the final compaction since the applied load was limited by the 330 μm spacer shims. Gels were weighed before and after compression to give % compaction. Loads and durations were between 10 and 50 g and from 10 seconds to 5 minutes. Construct thickness post compaction was measured directly from histological specimens in transverse section (stabilised control: 57%, compared to gels compressed to 87% and 91% by weight). For 'tension pre-alignment' compressed collagen sheets (with or without cells) were clamped horizontally in a culture chamber (6-7 mm clamp overlap at each end) and strained to 25%, over ~1 min using a screw thread displacement. Strained gels were fixed for microscopy in 4% paraformaldehyde in 0.1 M sodium cacodylate buffer pH 7.4.

Spiral Assembly of Collagen Sheets and Composites

PC collagen sheets were rolled off their nylon mesh along their short axis immediately after compression, to produce a tight spirally wound rod, 13 mm×1.75 mm diameter (FIG. 2a). Collagen:fibronectin (Fn) and collagen:hydroxyapatite (HA), were used as examples of heterogeneous spiral assembly. Orientated fibronectin mats were prepared in a stirred ultrafiltration cell as previously described[23]. Briefly, plasma fibronectin[19] (Fn: 1-2 mg·mL$^{-1}$ in 2 M urea. Bio-Products Lab, Elstree UK) was concentrated in a stirred ultrafiltration cell at 4° C. (10 kDa molecular weight cut membrane—Millipore, Watford, UK.). Resultant Fn mats were rinsed, freeze dried and rehydrated just prior to co-compression. The collagen gel was positioned to be off-set with the Fn mat (partially covering) in the compaction stack. Spiral assembly of the composite was the same as before, starting with the off-set Fn edge. For the collagen:HA exemplar, approx. 200 mg of HA granules (106-180 μm.: kindly donated by Plasma Biotal Ltd., Derbyshire, UK), were spread evenly over the surface of the long edges of a freshly cast collagen gel (to a width of 5 mm). Compaction of this construct type was used only blotting of fluid to the underlying paper layer, without any upper nylon mesh or load. Spiral assembly of this construct (around its short edge) gave a dense collagen cable with hard, HA embedded, compacted end-pieces.

Mechanical Testing

Mechanical testing of single PC collagen sheets was unreliable due to their thin structure (20-40 μm) and spiral assembled constructs were used throughout. Constructs, stored in EBSS prior to testing, were clamped at each end using 2 mm strips of thin steel mesh reinforced by cyanoacrylate super-gluing, mounted into a Dynamic Mechanical Analyser (DMA-7e: Perkin Elmer, Buckinghamshire, UK).

Mechanical testing was carried out under uniaxial tension at a loading rate of 200 mN·min$^{-1}$. (stress rate of 83 KPa·min$^{-1}$), until failure, with constant sample hydration by application of buffer. Quasi-dynamic stress-strain values for each mechanical test were acquired by the DMA-7e linked Pyris™ version 5.02 software (Perkin Elmer, Buckinghamshire, UK). Statistical analysis was on Microsoft Excel™ software.

Imaging and Image Analysis

Light Microscopy specimens were fixed with 4% paraformaldehyde in 0.1 M sodium cacodylate buffer pH 7.4 for routine wax embedding and sectioning (5-8 μm) and Haematoxylin/Eosin (H&E) or Picro-Sirius Red staining (to enhance collagen fibril birefringence). Specimens were examined on an Olympus BH-2 photo-microscope. Transmission Electron Microscopy (TEM) for analysis of collagen fibril density PC constructs (93% compressed) were fixed in 4% paraformaldehyde, 0.1 M sodium cacodylate buffer pH 7.4 and 2% glutaraldehyde and rinsed in the cacodylate buffer prior to treatment with 1% (w/v) osmium tetroxide, routine dehydration and embedding in Spurr's resin (Agar Scientific, Stansted, UK) and ultra-thin sectioning. Stained sections (2% (w/v) uranyl nitrate and Reynold's Lead Citrate) were viewed in a Philips CM12 instrument. Random images from the edge and gel body regions of replicate PC constructs (same magnification) were digitised and outlined to determining the % total field area occupied by collagen fibrils (i.e. fibril density determination).

Analysis of captured images used Openlab™ version 3.1.5 image analysis software (Improvision™, Coventry, UK). Statistically analysed used Graphpad Prism™ software, version 4 (GraphPad Software™, San Diego, USA). For Scanning Electron Microscopy (SEM), PC constructs were fixed in 4% paraformaldehyde (in 0.1 M Na cacodylate buffer pH 7.4; 2 h), further fixed in 1% tannic acid (w/v) in 0.05 M Na cacodylate buffer (1 h.) and dehydrated through an alcohol series to hexamethyldisilazane (HMDS) with air drying. Dry specimens were torn to reveal internal structure along one edge, gold palladium sputter coated and viewed in a Joel 5500LV SEM (L. Wollweber et al *J. Microsc.* 1981, 121, 185).

Results

Plastic Compression

Figure 2:
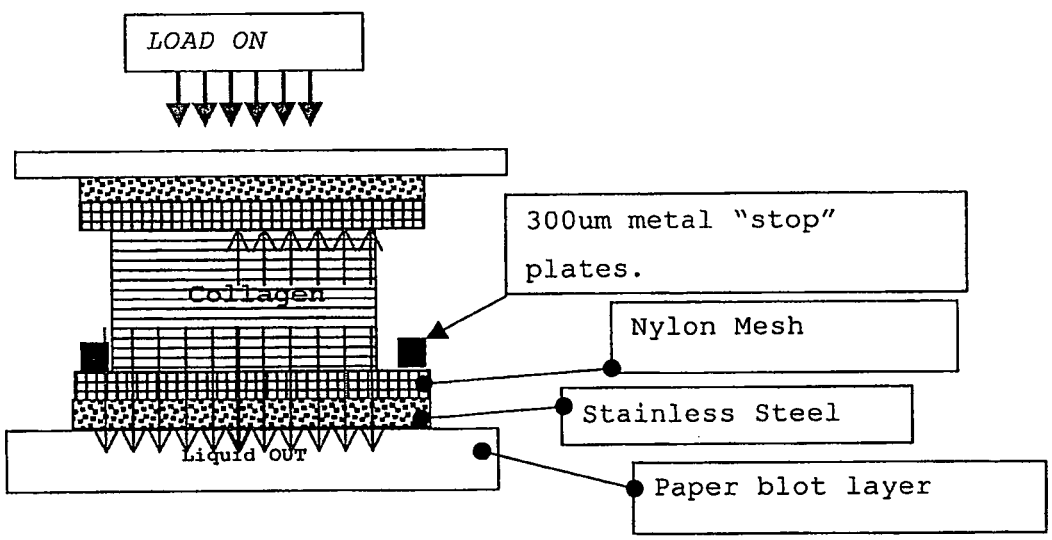
FIG. 2 shows combined plastic compression and blotting of a gel.

Collagen gels with embedded cells (total 1 million) were compressed using a system as shown in FIGS. 1 and 2, using a dead weight (50 g) and porous paper removal of expelled liquid. The cast gels were 13 mm wide by 33 mm long and ~4 mm deep. Although compression was almost the same at 1 and 5 minutes, a standardised compaction time of 5 min was used. The 'stop' shims were designed to leave a PC construct of 300 μm thick (i.e. 10× compression) but it was found that the process ran over because of the capillary action of the large porous paper sheet, such that final sheet constructs were 30-50 μm thick when measured. This represents a >100 fold compression in scale (from about 1.72 ml to 0.0172 ml).

The initial concentration of cells in the gel was about $5.8\times10^5$/ml and this increased to $5.8\times10^7$/ml after compaction. Assuming that the cells were spherical with a 10 μm radius, cells made up about 0.18% v/v of the starting gel and 18% v/v of the final sheet construct. Of course, larger cells at the same density would represent a greater proportion of the construct and smaller cells would represent a smaller proportion.

Composition of Constructs

At the end of the compression process (5 min; 50 gm) the cell density was about 15-20% by volume of the total construct (assumed spherical, nominal volume cells). At this stage, the total loss of fluid was determined by weight as 98.4% with a wet weight of sheet construct of 43.5 mg. A gel that was air-dried at 37° C. for 24 hours weighed 5.4 mg, indicating that the sheet construct comprises 18% collagen and 82% fluid. A base composition of 15-20% v/v cells (assuming spherical cells of 10 µm radius), ~20% collagen and the balance water is comparable with some simple or natural tissues. For spherical cells of 5 µm radius, the cell content falls to 2% v/v.

Cell Viability and Culture of Constructs

A construct comprising live rat tendon fibroblasts in collagen gel was assembled and compressed as described above.

Viability of the fibroblasts was determined accurately immediately following compression (at the 40 um thick sheet stage). A dual fluorescent staining technique was employed in which the construct culture was treated with 1 µm ethidium homodimer plus 1 µm calcein AM in DMEM culture medium for 1 hour at 37 degrees C. This deposits red fluorochrome in the nuclei of dead cells and makes living cytoplasm fluoresce green (respectively) when viewed in a fluorescence microscope. Random fields were photographed (under 40× objective in all cases) across the construct, (containing 2-300 cell total each) and red and green fluorescent cells counted in each field in the photographs with the aid of a 25 mm grid. Ratios of live/dead cells were determined from ~4000 cells from 15-20 fields/determination and expressed as mean % viability+/−SD (Table 2)

The gelling process itself (full hydration) had no significant effect on cell viability and there was little effect (~10% loss) on cell viability. Even at the relatively high rate of compression/shrinkage of the constructs used here (100 fold reduction in 5 min) there was only a small fall in viability (~6%) during plastic compression with no additional loss due to the tension-alignment stage. However, the compressed constructs were in the form of sheets of around 40 µm thick and as a result very sensitive to dehydration. Table 2 shows the rapid loss of cell viability observed due to dehydration when simply held in flowing, room temperature air in the sterile flow hood (20 sec. and 1 min. respectively). This produced ~70% cell death at 20 sec. and complete loss of viability (i.e. total desiccation) after only 1 min. At this stage, procedures carried out either under liquid (medium/PBS) or in a 100% humid chamber will reduce cell death.

Note that in experiments in which more controlled thickness was needed, the paper blot was removed and the process carried out with dead weight only, under culture medium.

Gel Maturation

Non-compressed collagen gels were considered 'unstable materials' outside of their aqueous environment as any form of lifting/manipulation caused liquid to be lost and so their density/properties to change. The extent of instability was studied in terms of the rates of early liquid loss by simply leaving the gels on either a flat or 45 degree inclined nonporous plate in a humid (100%) chamber.

Figure 3:
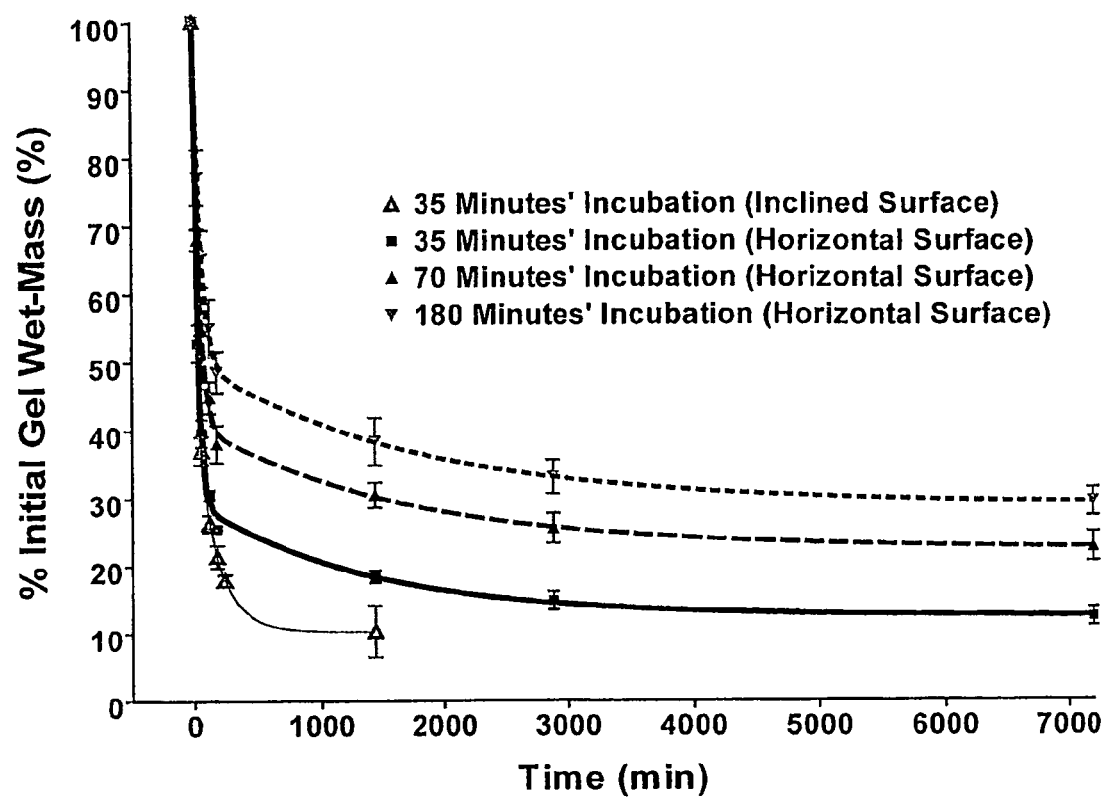
FIG. 3 shows a graph of the reduction in gel mass (i.e. % fluid loss) for self-compression of gels: under their own weight: with increasing pre-compression gelling times: for horizontal and 45° inclined gels (points are mean±SD, n=3)

FIG. 3 shows the loss of mass (fluid) over time, for gels after increasing incubation periods at 37° C. (collagen gels continue to stabilise for approx. 2 h after initial solidification) . The precipitous fall in mass over the first 2 hours demonstrated their intrinsic mechanical instability once removed from liquid. Self-compression fell off suddenly to a slow compaction rate at a hydration level which correlated with the length of the stabilisation period.

Tilting the gel angle to 45° during self-compression to enhance the flow-gradient, increased the duration of the initial rapid compaction (FIG. 3) and significantly greater level of plastic compression. Self-compression for 180 min, resulting in ~57% reduction in mass, was used to produce stabilised 'control' gels.

Construct Dehydration/Water Loss in Air

Figure 4:
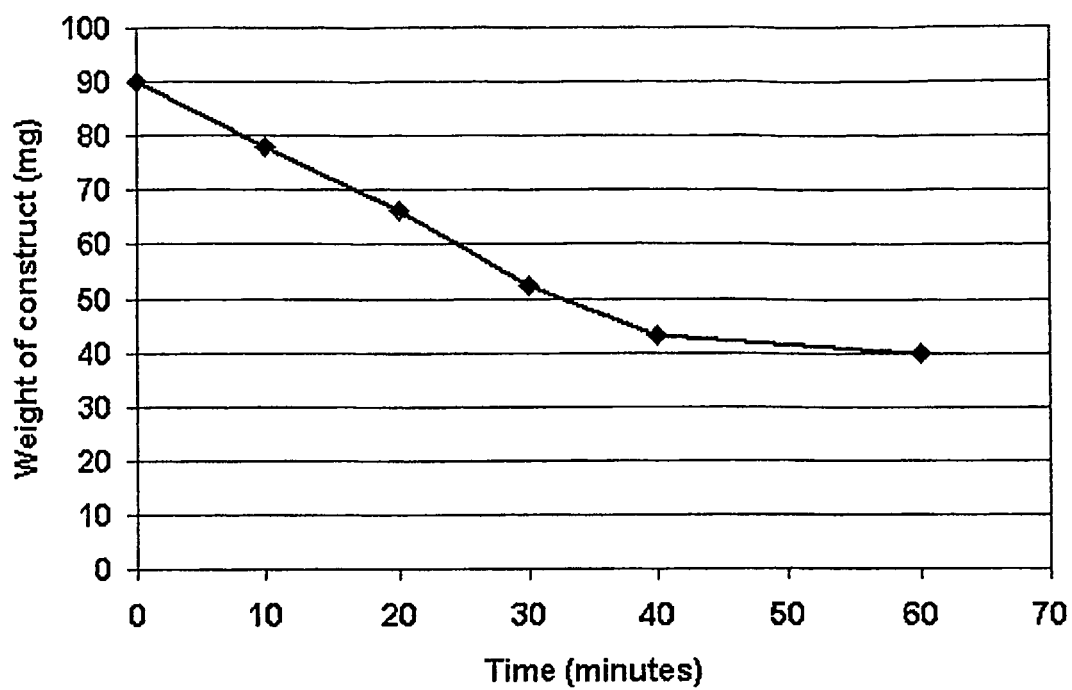
FIG. 4 shows the water loss from consolidated constructs in air.

Cell free collagen constructs (in this case compressed 40 µm sheets, prior to rolling) were freshly prepared as above (mean of 3) and left in air (no flow, room temp.) on a fine balance to measure the rate of water loss through evaporation, measuring the fall in weight (FIG. 4). Weight loss was linear for the first stage and the inflection point of the curve (~42 min) indicated that near complete dehydration was reached after only 40 min. (note in still air with no desiccating agent). This reflects the expected time for air-drying.

Alignment in Compacted Constructs

A standard hydrated collagen gel was prepared as described above and subjected to plastic compression.

Part-way through the plastic compression process, the gel was placed under uniaxial tensile load (25% strain) and then returned to the plastic compression regime. The fibril alignment induced by the tensile strain was observed to be fixed in the gel by the plastic compression, providing an aligned, dense composite. Cells seeded in the gel at the start of the process were alive in the completed composite.

Scanning Electron Microscopy of Collagen PC Sheets with Tensile Pre-Alignment.

The appearance of cell-free collagen PC constructs (sheet form) after tension pre-alignment of collagen fibrils by application of a uniaxial tensile loading to give a total 25% applied strain was examined using Scanning Electron microscopy. Specimens were fixed in glutaraldehyde, mounted onto SEM stubs, critical point dried and sputter coated with gold as for routine SEM, prior to examination in a JOEL semi environmental SEM.

Figure 5:
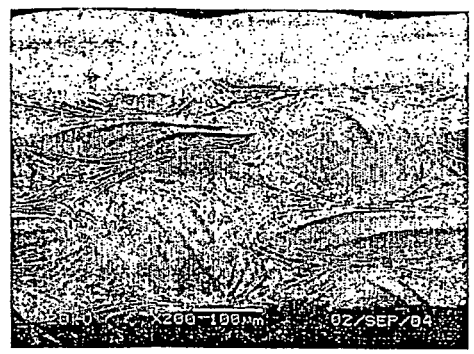
FIG. 5 shows a scanning electron micrograph of the compressed construct without (top panel) after (bottom panel) tension pre-alignment with 25% uniaxial strain. (white bars=100 µm in both micrographs).
Figure 5:

FIG. 5 (top panel) shows the post compression surface topography with a firmly embossed pattern of the nylon support mesh (with fibrous structure from <1 to >100 µm). The surface of the material was observed to be composed of thick parallel fibres of collagen (many times increased over the starting collagen fibril diameter of ~50-100 nm diameter). Application of uniaxial strain of 25% realigned this embossed pattern into surface grooves, parallel with the applied strain. Since the process was one of plastic deformation, re-structuring of the surface was also plastic resulting in a stable, imprinted topography, controlled by combinations of embossing and tension pre-alignment. Consequently, this µm and sub-µm anisotropic pattern was stable after removal of the applied tension and the directional lamellar structure comprising compressed collagen fibrils was also visible (FIG. 5 (bottom panel)).

Effect of Blotting

The relative importance of liquid uptake (blotting) by the two porous layers (paper and nylon) was investigated.

Figure 6:
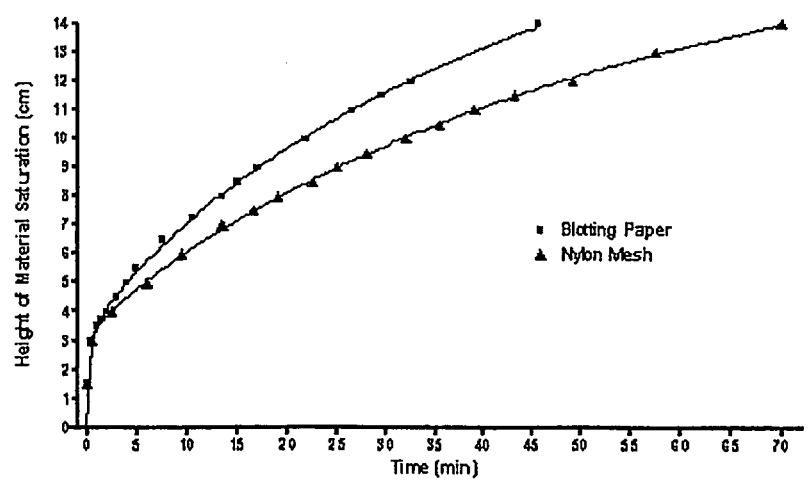
FIG. 6 shows the relative importance of liquid uptake (blotting) by paper and nylon porous layers.

Rectangular strips of the 2 materials were held upright in a PBS solution containing blue dye (for ease of visualisation) and the height to which each liquid front rose was measured over time. The results are shown in FIG. 6.

Whilst differences were observed in the pattern of liquid uptake by the two materials, both were capable of contributing significantly to the blotting effect.

In some experiments herein, the paper layer was removed in order to reduce the contribution of blotting to the overall fluid removal.

This reduces rather than abrogates the blotting effect. Hence compression carried out with paper under layer was referred to as enhanced blotting procedure. Non-enhanced compression was carried out using the nylon layer only.

Compression performed under liquid, for example to reduce desiccation, completely eliminated the blotting effect.

Compression Conditions

Replicate collagen gels were compressed (without enhanced blotting) under a range of dead weight loads and times of compression, without the blotting of the porous paper layer. In each case, the starting and completed (compressed) weights of the constructs were measured to give % decrease in gel weight and the results shown in FIG. 7.

Figure 7:
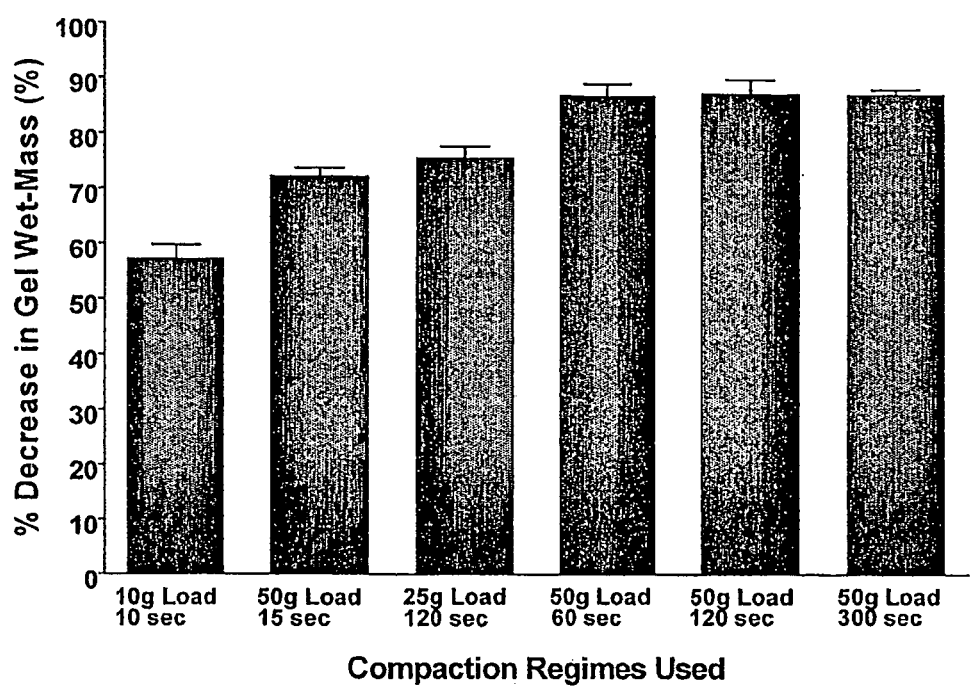
FIG. 7 shows the effect of compression of replicate collagen gels under a range of dead weight loads and times of compression.

Mean compression with 10 g loading for 10 sec. was 57%, which increased to 88% with application of 50 g for 1 min (FIG. 7). Little further compression was observed after 2 min using 50 g compression weight and extension of the compression period to 5 min did not increase fluid loss, although it did reduce inter-construct variance. The 50 g for 5 min. vertical compression protocol was adopted as the standardised method. This PC protocol reduced initial construct thickness from a gel of approximately 3.6 mm to a collagen sheet of 23-48 μm (Table 1), i.e. shrinkage factor was >2 orders of magnitude. Such collagen sheets were typically 18% collagen and 82% fluid. Collagen density rose with cell seeded constructs as this reduced the relative fluid content, with final cell densities of 10 to 20% (v/v), depending on the initial seeding density and unattached (spherical) cell diameter. These compositions were comparable to some pre-maturity connective tissues and would be suitable as early tissue grafts.

Compound effects were analysed by comparing the effect of 2 and 5 min compression with/without blotting enhancement. No additional compaction effect was observed with blotting enhancement, for either 2 or 5 min compression.

Collagen Fibril Density

The collagen fibril density of standard constructs (40 μm thick compressed sheets: 50 g for 5 min.) was determined relative to control constructs allowed to stabilise to ~50% of initial weight by leaving to compact under gravity on a flat plate in a humid chamber.

Fibril density was determined directly by image analysis of the collagen fibril area relative to (%) total field area from TEM images (all at the same magnification).

Collagen specimens were put through routine transmission electron microscope preparation, with glutaraldehyde fixation (2.5% in cacodylate buffer pH 7.5), embedding in Spurs resin, ultra thin transverse sectioning (through the 40 μm thickness) and routine staining with lead citrate prior to examination in a Philips CM12 microscope. High quality Photomicrographs were taken of random good quality fields from the test gels (for centre-edge comparisons 'centre' fields were taken randomly from either side of the mid line of the construct). These images were then scanned into an image analysis system (Improvision-Mackintosh, Birmingham, UK) and replicate collagen fibrils were outlined in replicate fields to distinguish the fibril areas from interfibrillar spaces. The image analysis mode then produced quantitative estimates of the % fibril densities per field. Median densities are presented with standard deviation and ranges (box & whisker plots). Comparison of densities between control and compressed constructs shows dramatic increases in fibril density.

Figure 8:
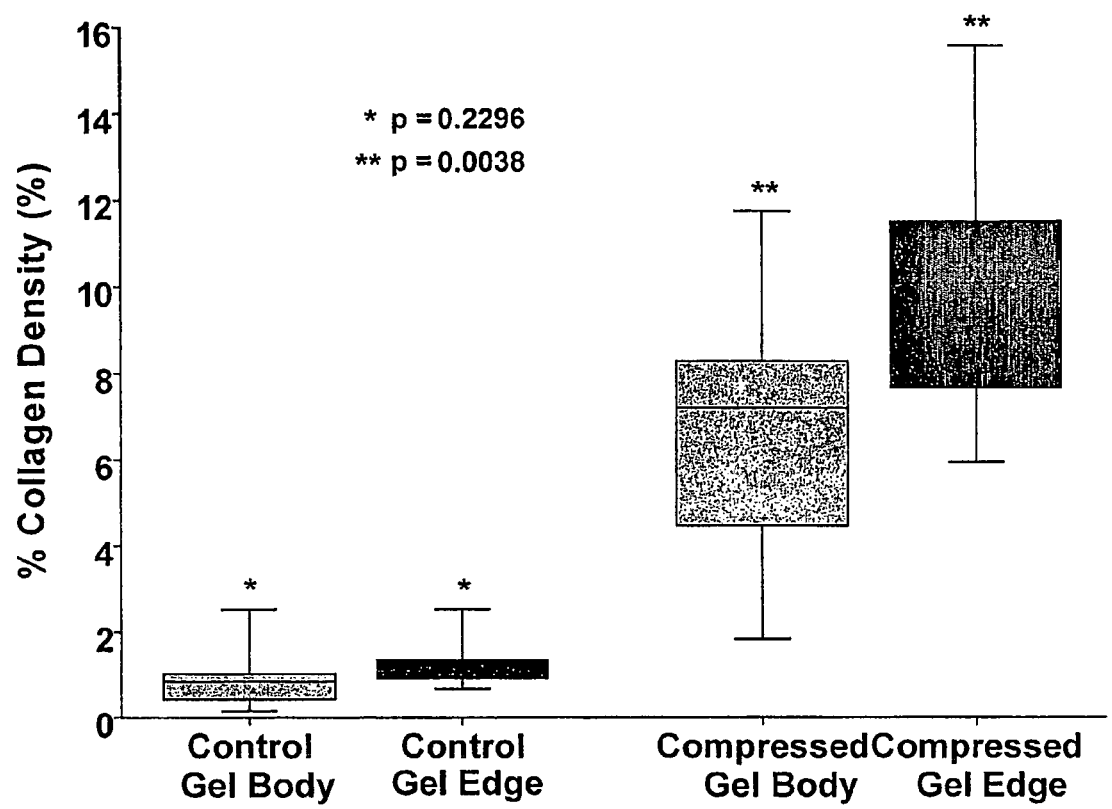
FIG. 8 shows differences in collagen fibril density in PC versus control cell-free constructs and between the edge and body of specimen sheets, assessed by image analysis of transmission electron micrographs (note: control gels were allowed to self-compress to 57%; PC constructs to 93%). The box and whisker plot shows median fibril densities, with overall (bar) and inter-quartile (box) ranges for edge versus body of control and PC constructs [mean control values were ~1% (difference not significant) and PC constructs were 9.9% (edge) and 6.6% respectively (p<0.005) n=13 to 17]. Fibril density increased 7-8 fold (* and **p<0.0001) between PC and control constructs in the respective areas.

Collagen fibril densities in the core and edge regions of compressed constructs, both without and with cells, were compared (FIG. 8). In both the edge and core regions, the collagen fibril density was higher in cellular constructs, as expected since the measurements excluded volume occupied by the cells (so this effectively displaced the collagen content). The increase was ~50% in the edge and 100% in the core regions, $p<0.002$ in both cases. Fibril density in the edge region of acellular constructs was approx 50% greater than that in the comparable core regions ($p=0.0038$). However, this difference completely disappeared in the cell-seeded constructs (apparently due to the sampling technique and the fact that the cells also segregate regionally). Segregation of collagen fibrils towards the construct edge (i.e. formation of lamellae or heterogeneities) occurred as predicted (above) based on the effective filtration behaviour of liquid from the surface of the collagen gel during compression and complete retention of collagen fibrils at that interface.

Tubular Constructs

Figure 9:
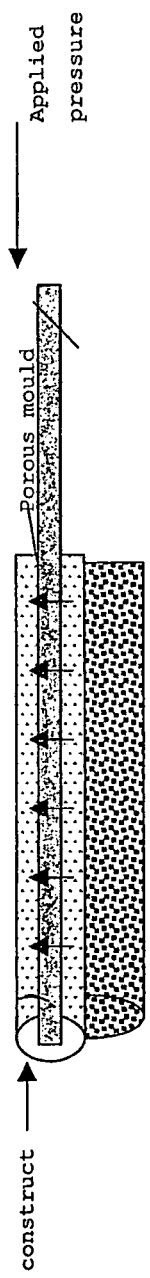
FIG. 9 shows an arrangement for providing a compressive impulse from the core of a structure to provide plastic compaction.

An alternative to the compression of the hyper-hydrated material (gel)-cell construct is to provide the compressive impulse from the core of the structure (FIG. 9). This may be useful, for example, for the formation of thin-walled tubes. The material (gel) device is formed over the outer surface of a cylindrical balloon such that inflation of the core balloon expands the construct (applying desirable mechanical loads where necessary), compressing its outer face against a porous (largely cylindrical) mould, thereby achieving controlled fluid expression. This is advantageous in terms of the dimensions of the layers produced (e.g. wide bore, thin wall), the layering structure, the fluid 'leaving' direction (i.e. microflow vector), and the application of mechanical forces to the resident cells and fibres in the support material (e.g. for aligning).

Continuous Flow Extrusion-Plastic Compression

Figure 10:
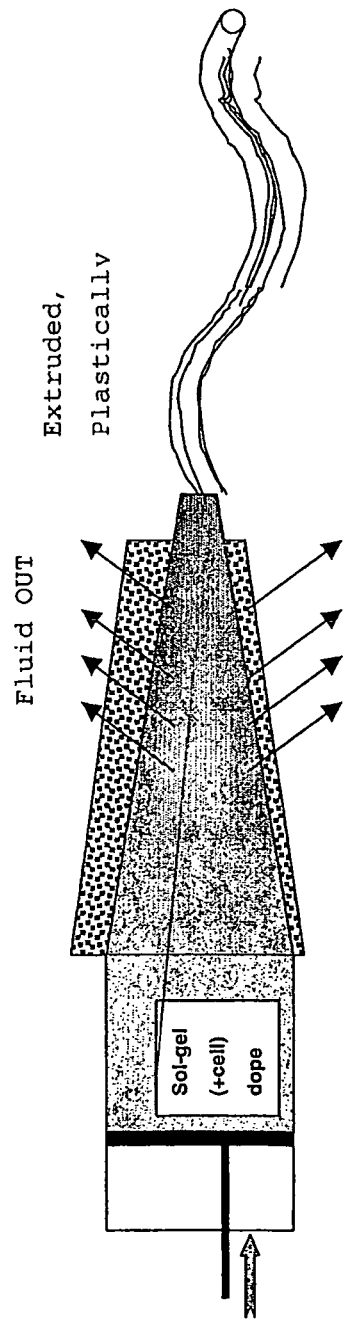
FIG. 10 shows a conical flow-chamber for continuous flow extrusion-plastic compression

Continuous flow extrusion-plastic compression may be achieved by fluid expression, tissue shrinkage/compaction through a conical flow-chamber (FIG. 10). A pre-gelling sol of the (collagen) dope preparation (with cells if needed) is treated so that it undergoes simultaneous increasing directional shear, concentration and fluid viscosity.

This can be achieved by taking advantage of the few minutes gelling time (which can be controlled extended by holding the temperature at 4° C. and raising to 37° C.). A pre-gelling solution of collagen (or other similar liquid crystal polymers, e.g. fibronectin, silk protein or fibrinogen) is prepared is slowly pumped along a narrowing conical chamber, the walls of which are porous, allowing expression of interstitial fluid. As the gel-sol fluid moves along the chamber it undergoes directional shear (aligning and aggregating polymer fibres); fluid is forced out of the dope into the porous walls (macromolecular polymers are retained by the semi-permeable lining membrane) compacting the material as it gels; the sol rapidly sets to form a gel which is rapidly compressed and consolidated as it is extruded from the distal, constricting orifice of the conical chamber. The result is an extruded, dense cable or thread of aligned 'tissue'.

Multiple Layer Constructs

Three fibroblast populated constructs (flat, rectangular collagen gels) were allowed to contract (non-external) in the uniaxial tethered configuration as described in Mudera et al. 2000, and Prajapati et al. 2000 for 16 hours to achieve cell and collagen fibril alignment. At time zero, each construct (or "leaflet") was approximately 3 mm thick, making a total thickness of 9 mm. At the completion of the contraction culture, each leaflet was 2 mm in thickness (6 mm in total).

The 3 leaflets were released from the tethers and placed into a 35 mm culture dish supported by (1) a coarse nylon mesh, (2) a sheet of 70 μm pore sterile filter membrane. The leaflets were then covered with DMEM culture medium (Dulbecco's modified Eagle's Medium) and placed under the compression platter of a Dartech mechanical testing rig, mounted in a 37° C., carbon dioxide cell culture incubator.

The triple leaflet construct was maintained over 5 days in culture such that the total construct was left at 1.5 mm thick (i.e. a total increase in density of 6 fold from both fibril alignment and plastic compression stages). The resulting construct was grossly denser (optically), stiffer and each of the 3 leaflets was firmly attached to its neighbour to give a fully integrated single construct.

This demonstrates the surprisingly efficient mechanisms of plastic compaction under compression to dehydrate the collagen fibril construct and integrate bioreactor sheets at the end of the culture period (to give desired thickness and physical strength). The resulting construct did not return to its original dimensions (i.e. no loss of density), contained living cells, and was mechanically integrated and strong.

Capillary Fibre Constructs

A standard hydrated collagen gel was prepared as described above. Fine glass fibres (35 micron diameter phosphate glass) were overlaid in a parallel arrangement on the surface of the collagen gel. A second collagen gel was formed over the surface of this composite, such that the whole structure was consolidated by plastic compression as described above.

The resulting material was observed to consist of a sandwich of biological material, containing living cells, traversed through its length by fine guiding fibres.

Bone Biomimetics

Figure 11:
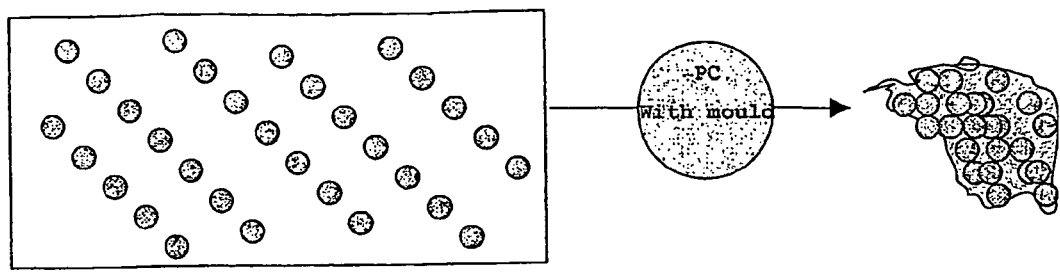
FIG. 11 shows the plastic compaction of a suspension of porous beads of standard mineralized tissue biomaterials into a collagen construct, as a biomimetic form of bone.

A standard hydrated collagen gel is prepared as described above except that a plurality of porous beads is dispersed amongst the fibres of the collagen scaffold (FIG. 11).

Figure 12:
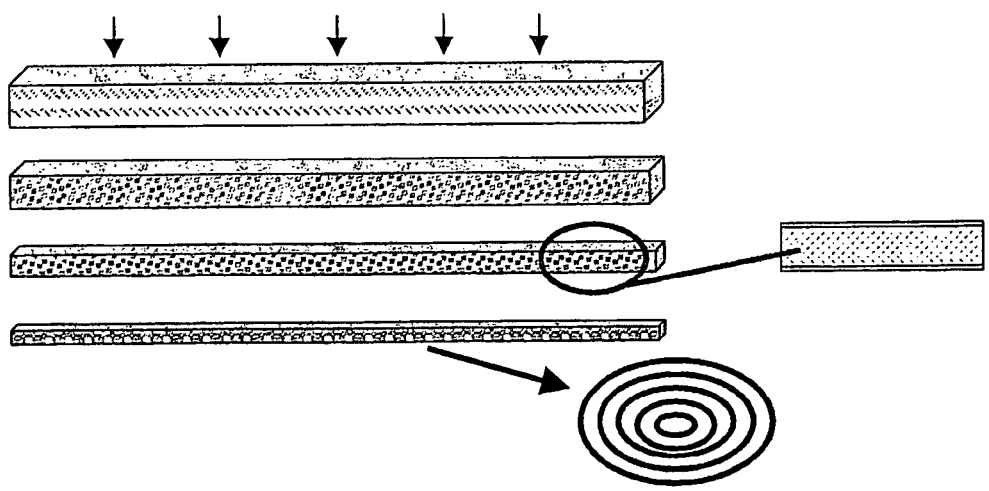
FIG. 12 shows a summary of the preparation and spiral assembly of PC constructed sheets into 3D structures, indicating the edge lamellae structure and spiral lamellae after rolling into 3D construct.

Compaction of the suspension of porous beads of standard mineralised tissue biomaterials in the collagen gel produces a material suitable for use as a biomimetic for bone Rolled Construct Fabrication Being around 30 μm in thickness, PC collagen sheets were difficult and fragile to handle, which led to the development of the spiral assembly stage (FIG. 12). This involved rolling up the sheet around its short axis to produce a 3D rod-like 'tissue' construct. Spirally assembled constructs were convenient for handling, culture and mechanical testing. The process was also used to generate complex meso-scale structures in 3D through stacking of the PC collagen layers, producing structures in the range of 10 to 100 μm.

Figure 13:
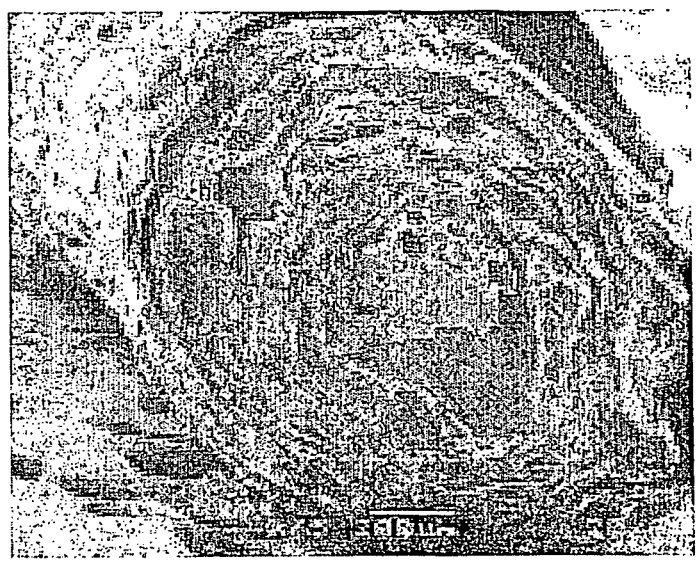
FIG. 13 shows scanning electron micrograph of end view of a spiraled construct showing collagen sheet layers (with interface shrinkage: ~2 mm diam FIG. 14 shows typical tensile test stress-strain curve from an acellular (zero time) spiral assembled construct showing the material behaviour to failure and a supplementary plot of modulus. Construct lines indicate the toe region, region of linear extension and yield point (leading to the break point)

A standardised spirally assembled construct was prepared as described herein from the initial gel (with or without cells) of 13 mm wide×33 mm long×~4 mm thick. Cell density was initially about $5.8 \times 10^5$ per ml and increased to $5.8 \times 10^7$ after compaction. After reduction of the thickness to between 30 and 50 μm by the plastic compression, the sheets were rolled, into spiral assembled rods, along their shorter (13 mm) edge to give a construct of 13 mm long by 1.75 mm diameter. An SEM across the end of the construct (bar=200 μm) is shown in FIG. 13.

In addition, histological analysis of the spirally assembled constructs showed that cells were viable, living and active many weeks after the construct was placed into culture.

Histological Analysis of Rolled Constructs

Rolled spiral constructs were formed from random orientated collagen gels (i.e. not tension pre-aligned). The structure and cell characteristics of these constructs were examined histologically at various time points by standard techniques (i.e. routine formalin fixation in cacodylate buffer, wax embedding, sectioning (both parallel and perpendicular to the long axis) with H&E staining).

Neo-tissues at zero time (immediately after compression) contained dense, evenly spaced cells of normal, viable appearance. The compression process also produced, smaller scale structures (i.e. <10 μm) within the 30-μm sheets. This 'structuring' consisted of compacted lamellae of collagen fibrils, parallel with the fluid leaving surfaces (FLS), in this case the basal surface. This was the consequence of the directional egress of fluid, predominantly from a single surface. In effect, the particular material (collagen fibrils and cells) was retained at the leaving interface, rather like the compaction of material at a filtration surface. Fine collagen lamellae (<1 μm thick) were evident throughout the depth of the compressed collagen sheet but by far the largest, densest layer formed at the fluid leaving surface, as seen in the birefringence pattern, and parallel to it.

Cells within the compressed sheets were observed to align with these lamellae. Prior to spiral assembly, resident cells appeared normal and active, spreading through and attaching to the collagen substrate by 3 hours in culture After 0 and 14 days in culture (free floating in DMEM culture medium, 10% foetal calf serum, 37 degrees C., under 5% $CO_2$ incubator) these cells were spread and attached to the matrix taking on the normal 3D appearance of fibroblasts in a tissue, with even distribution and no obvious loss of activity, viability or cell death. At the 14-day stage, cells were elongate or discoid lying within collagen lamellae of the rolled construct.

After 5 weeks in culture (untethered), a dense, viable cell distribution through the full thickness of the construct (i.e. no cell-free core) was observed. There were signs of new tissue formation by resident cells over the construct surface and at its ends and with this, distinct areas of layering and structure, such that the core matrix and cells were generally orientated longitudinally whilst the outer cell layers were more circumferential (confirmed by comparing sections of the same construct in parallel and perpendicular planes). The construct ends, at this stage, were relatively irregular disorganised outgrowths. Distinct cellularised lamellae (with intervening channels) were evident between apparent tissue layers at this stage, though it was not clear when these were formed. Prominent layering of collagen was evident in sheets around the construct and resident flattened discoid cells lay within the collagen layers. The 5 weeks constructs were thus morphologically comparable with early natural connective tissues with healthy cells embedded in and between many layers of collagen fibres.

Thus cells were clearly viable and attached, within a dense 3D matrix over the entire culture period. The structure of the matrix changed gradually over longer culture period (in terms of apparent cell/matrix outgrowth over the surface and the formation of channels within the core) but remained generally constant with dense connective tissue surrounding active live cells distributed throughout the construct (i.e. including the core).

Mechanical Properties of Rolled Constructs

Having established that the constructs remain viable and cellularised (with a dense matrix) for days and weeks after construction, the mechanical properties of the constructs were tested as described above.

Figure 14:
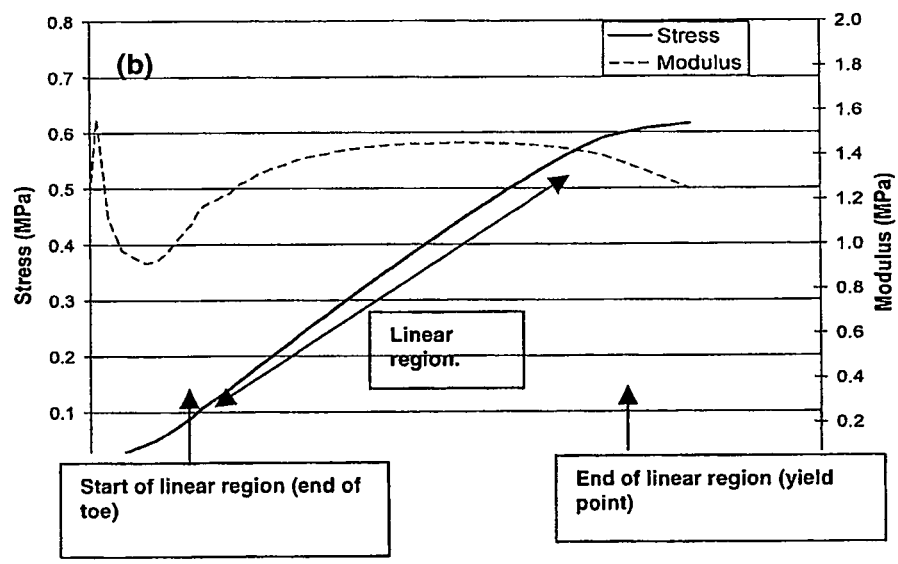

FIG. 14 shows a typical tensile test stress-strain curve from an acellular (zero time) spiral assembled construct showing the material behaviour to failure and a supplementary plot of modulus. Construct lines indicate the toe region, region of linear extension and yield point (leading to the break point). Cellular gels were observed to have a reduced or absent toe region, and decreased stress and strain to fail relative to acellular gels.

The cell element of the cellular gels comprised a substantial part of the construct total volume and this fraction was clearly weaker than the compressed collagen matrix.

Acellular constructs produced through the standard PC technique (50 g for 5 min) had functionally useful mean tensile break-strength (0.6 MPa±0.11) with a modulus of 1.5 MPa±0.36 which did not significantly change after 2 weeks in culture. Seeding constructs with fibroblasts resulted in high cell-densities post PC and not surprisingly this reduced the yield-strength and modulus by 71 and 34% respectively (FIG. 15), and abolished the toe-region at zero time culture point (FIG. 16). Whilst the modulus was reduced by a third, break stress was almost unchanged by cell seeding (0.55 MPa±0.06)

Figure 15:
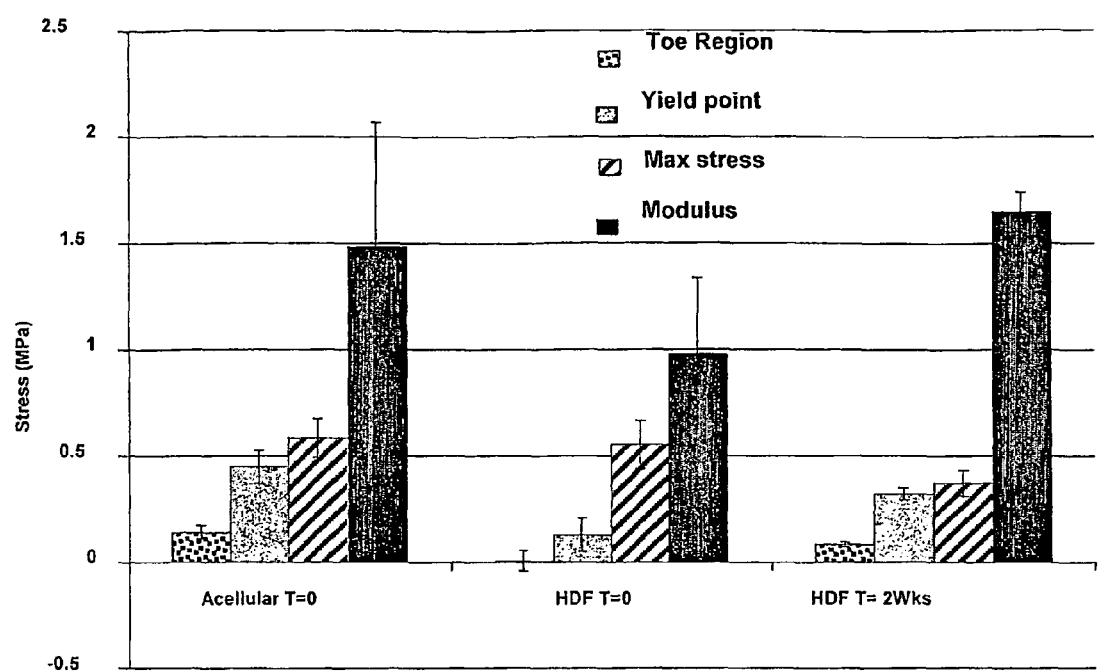
FIG. 15 shows a histogram (mean±SD; n=6-8) of toe, yield, max. break stress and modulus for cellular and acellular spiral constructs.
Figure 16:
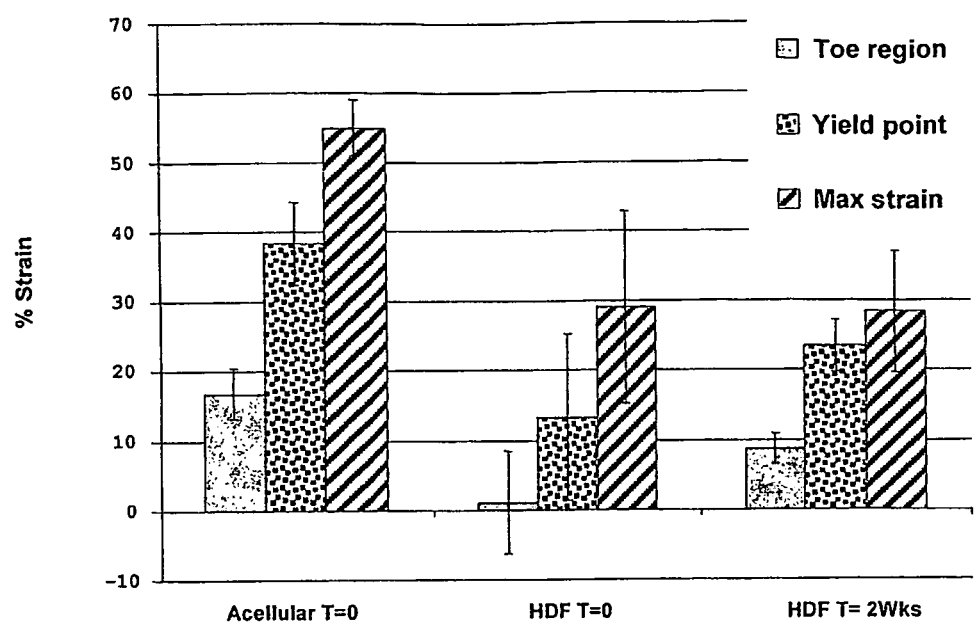
FIG. 16 shows the histogram for strain values of the toe region, yield and max. break points. Test constructs were either acellular or seeded with human dermal fibroblasts (HDF), cultured for zero or 2 weeks.

FIGS. 15 and 16 show the summary of mean break strengths and elastic moduli for both cellular and acellular constructs (mean+/−SD) at time zero and for cellular constructs at 2 weeks.

After 2 weeks in culture, cellular-construct material properties had improved almost to those of cell-free constructs, clear evidence of functional cellular remodelling of the new collagen scaffold. Yield stress and modulus both increased (approx. 1.5 and 2 fold respectively) over the cellular construct at zero time, while the break stress remained the same. A significant toe strain reappeared (almost lost—2%—from acellular gels) and the yield strain rose from 13 to 23%.

These data are for constructs prepared without tension pre-alignment of the collagen fibril. Strain to failure would be dramatically reduced (from the high level of 50%) for pre-aligned constructs where loading was parallel to the collagen fibril orientation.

Double Compression

Collagen roll (i.e. spiral) constructs produced as described above were subjected to compression for a second time (secondary compression) using similar techniques to produce a flat strap of dense collagenous material.

Cell and collagen density was found to be proportional to the loss of fluid. The average weight loss (so fluid expulsion) due to second compression was approximately 60% (of the spiral construct).

Figure 17:
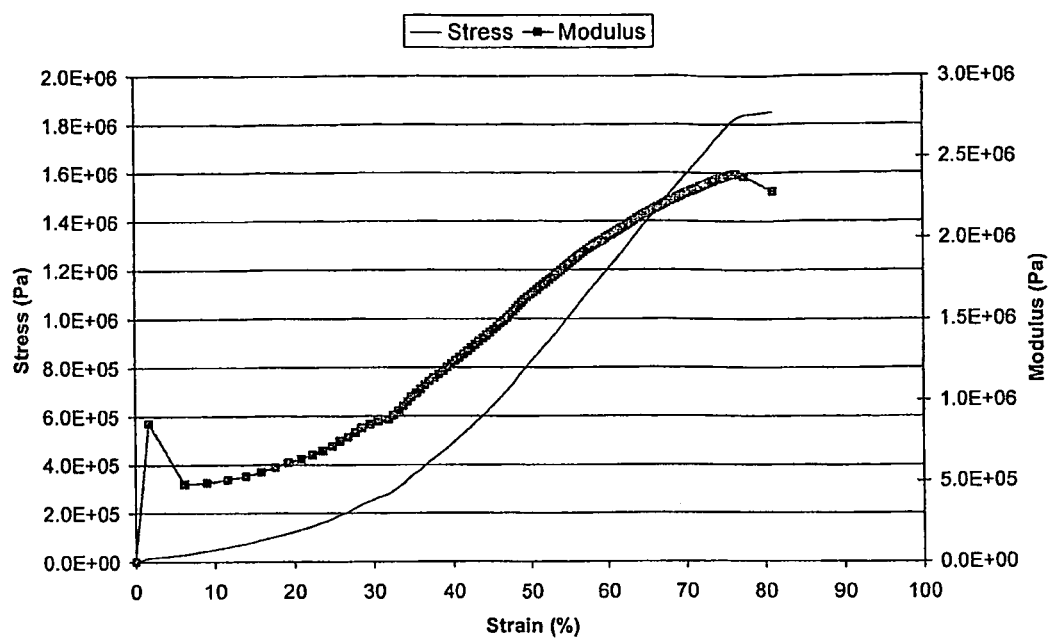
FIG. 17 shows Tensile Stress Strain behaviour of secondary compressed collagen gels.

The mechanical properties of the construct were tested as described above and the results shown in FIG. 17.

The Break Stress was found to be approaching 2 MPa, the modulus approaching 2.5 MPa and the Strain at break was up to 70%. Thus, secondary compression was found to further improve the mechanical properties of the construct.

Compression of the spiral rods in the orthogonal plane (ie. parallel to their long axis) produced similar compression properties and the material result was a flattened disc of collagen.

Nano-Micro-Scale Structure and Heterogeneous Layering

Figure 18:
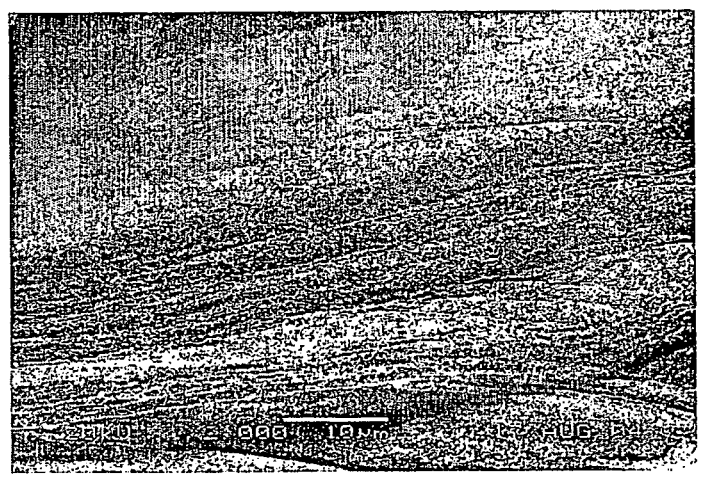
FIG. 18 shows the SEM appearance of a multi-lamella structure within a single (30 µm) PC collagen sheet, commonly being <1 to 2 µm in thickness.

Two further levels of organisation within which the 3D structure were found to be controllably generated by the methods described herein. Lamella formation were predicted due to fluid filtration from 'fluid leaving surfaces,' and first identified by their birefringence under polarised illumination. Lamellae were also seen under TEM and were measurable as differences in mean collagen fibril density between the edge and body of the matrix (FIG. 18). The lamellae were always parallel with the main fluid leaving surface. Not only was a 7-8-fold increase observed in mean fibril density between stable control and PC treated constructs, but there was a significant increase in fibril density between the construct edge and body.

Figure 19:
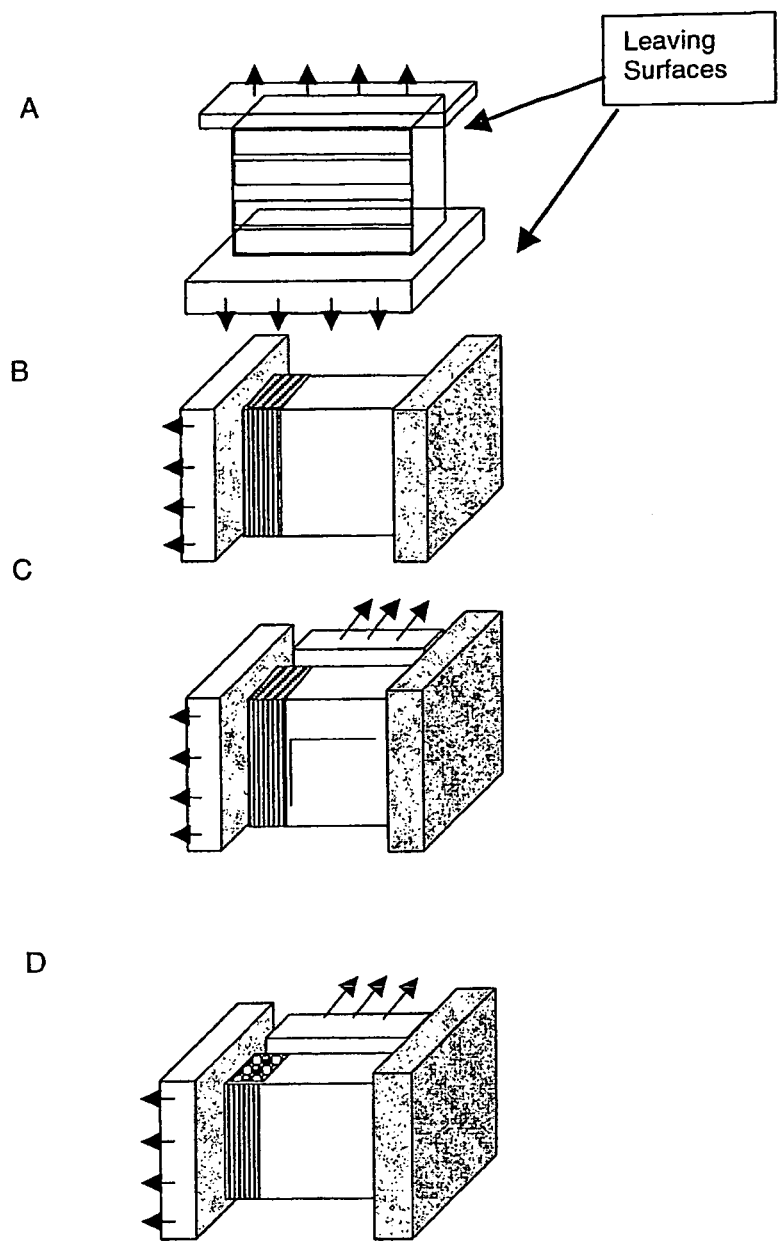
FIG. 19 shows a diagram indicating the variation of mesostructure (lamellae) which can be generated by controlling the fluid-leaving surface and the fluid leaving direction during Plastic compression. Clear plates represent porous, absorbent surfaces and the shaded plates represent impervious sheets, allowing no fluid flow.

The variation in orientation and position of meso-structure (lamellae) which can be generated by controlling the fluid-leaving surface and the fluid leaving direction during plastic compression is shown in FIG. 19.

Orientated collagen lamellae form adjacent to and parallel with the fluid leaving surfaces (against the porous layers) but less so next to impervious layers, generating a simple asymmetry) (FIGS. 19A and B). A second flow vector perpendicular to the first may be used to compact the lamellae in a second plane (FIG. 19C). This may produce a parallel (uniaxial) fibre bundle orientation (shown in FIG. 19D) from the compacted lamellae formed in FIG. 19C. In FIGS. 19A and 19B, the collagen lamellae would comprise of fibrils packed parallel to the leaving-surface but randomly orientated in the perpendicular plane. Simultaneous, biaxial fluid withdrawal, as shown in FIG. 19D would generate two planes of symmetry, further compacting the collagen lamellae perpendicular to that shown in FIG. 19B, to produce a structure comparable to natural collagen fibril bundles. Combinations of blotting layers and single plane compressive loading may be used to control flow rate.

Figure 20:
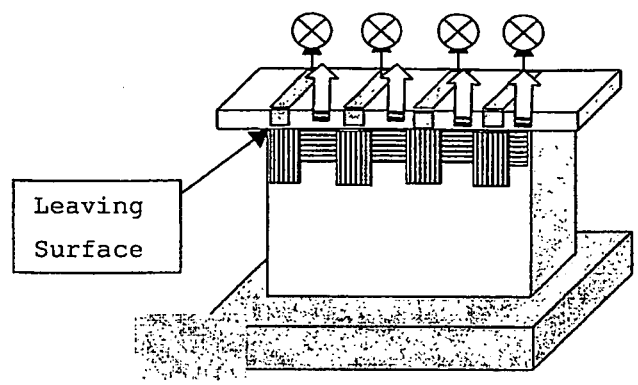
FIG. 20 shows the effects of localised perturbations in fluid flow vector. Clear plates represent porous, absorbent surfaces and the shaded plates represent impervious sheets, allowing no fluid flow
Figure 20:
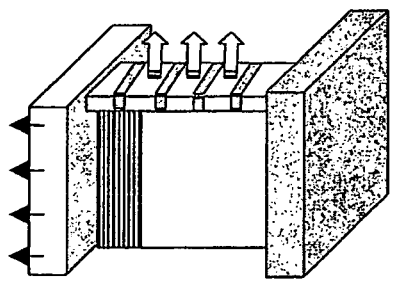

The effects of localised perturbations in fluid flow vector are shown in FIG. 20. FIG. 20A shows a modification of the porous blotting layer (upper face of the gel here) containing alternating porous [⋔] and non-porous [⊕] stripes, which are pressed onto the gel surface (non-porous patches may be produced for example, by painting with varnish). Liquid under the non-porous patches will be forced to flow parallel with the leaving surface, tending to form 'partial' lamellae perpendicular to the surface. However, below porous parts this displaced fluid flow will merge with the main, perpendicular outgoing flow, forming the conventional lamellae, parallel with the leaving surface. This will produce an orthogonal pattern of lamellae (with transition zones), effectively producing channels through the surface collagen sheet. Such channeling has guiding potential for pre-patterning of nerve, vessel or epithelial ingrowth. Different non-porous patterns (eg. discs) may be employed, for example, in combination with a second, perpendicular leaving surface, to modulate lamellar and channel structure (FIG. 20B). Again, compression is applied in one plane to control rate of flow.

Figure 21:
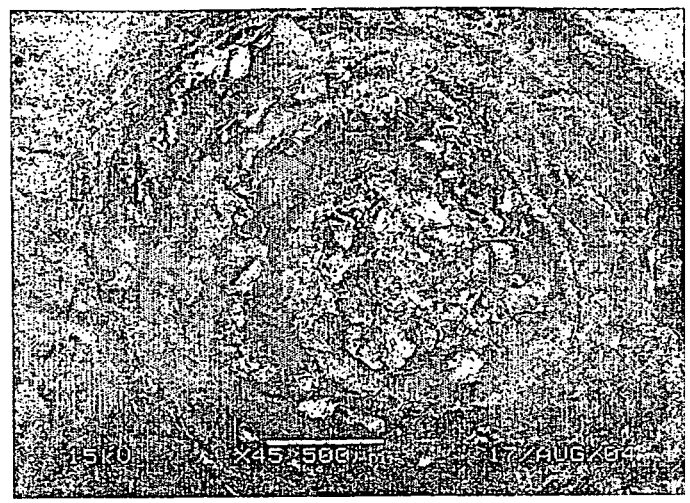
FIG. 21 shows scanning electron micrograph of end view of a spiraled construct showing collagen sheet layers (with interface shrinkage: ~2 mm diam) reinforced by hydroxyapatite granules.
Figure 22:
FIG. 22 shows scanning electron micrograph of end view of a spiraled construct showing collagen sheet layers (with interface shrinkage: ~2 mm diam) reinforced by soluble glass fibres (arrow-head).

Spiral assembly incorporated this meso-scale structure into a second level of spatial organisation at the scale of 100 s of microns. Composite PC constructs were fabricated by addition of either fibronectin (Fn) or hydroxyapatite (HA) granules. The hydrated Fn material also underwent plastic compression, though to a smaller extent than the collagen. A layer of fibrous Fn was co-compressed into collagen and the two layers were rolled together in an offset spiral to produce an outer collagen tube or sheath around a Fn core, with good integration between the layers. Structural complexity was also controllable to form zones along the length of the construct, as illustrated by the formation of 'hard tissue' ends to the construct. This was achieved by placing a layer of HA granules along the long edges of the gel surface before compression. Spiraling of this structure around the short edge produced a 'ligament model', with hard nodules at either end of a collagen cable. The transverse view of the composite (FIG. 21) shows the HA granules, packed between concentric collagen layers. The hydroxyapatite (HA) end zones allow excellent fixation to mechano-bioreactors and as well as allowing fixing (e.g. screwing) to bone in vivo.

These examples with or without cells illustrate the spatial and compositional range of possibilities for fabrication of meso-scale structures.

Complex Assemblies

As described above, multiple layers of prefabricated thin cellular sheets with a range of properties and contents may be assembled. These elements are themselves prefabricated in part using plastic compression to gain scale strength and tissue composition advantage. The elements take advantage of the spiral assembly approach to achieve micro (meso)-scale spatial biocomplexity with final stage compression to bond the elements together. For example, for a neural repair implant, a strong outer sheath may be provided with a non-adhesive external surface, inbuilt on and off ramps (to promote cell (neurite) survival, ingrowth and later outgrowth and reintegration) and micro-depots of graded growth factor content are built into the core sections.

Figure 23:
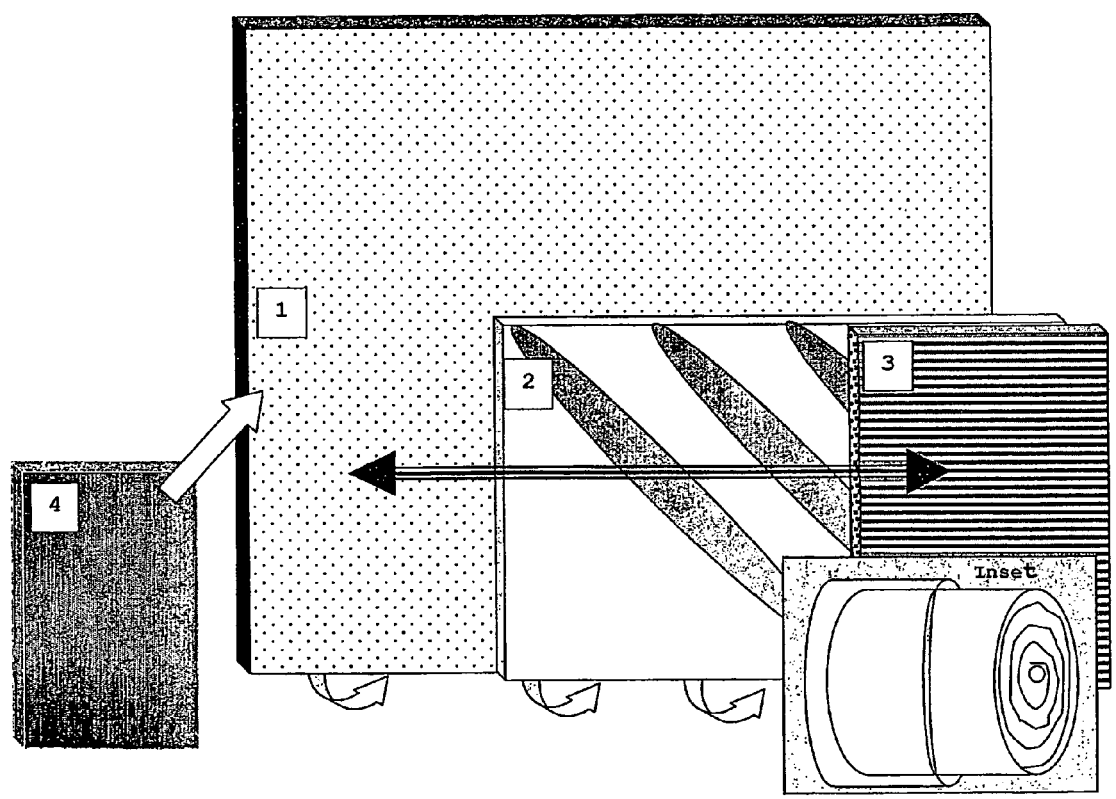
FIG. 23 shows a schematic of a generic 'layered' design for spiral auto assembly of complex nerve implant constructs.

FIG. 23 shows the concentric, spiral assembly of such a neural implant. The concentric axis defines the regenerate growth axis (2-headed arrow). Each element or functional modality of the final construct (sheath, axon guide filaments, sustained release depot, specialist ramps etc.) is fabricated either as a sheet (<50 μm thick, i.e. cell dimensions) or as inter-sheet fibre inserts. The cutaway example has an outer cell-seeded layer [1] (ideally with slow release of hyaluronan, for anti-adhesion) followed by a growth factor depot impregnated sheet [2] in which growth factors etc (depots with different compositions) are encapsulated. A sheet of conventional fibrillar axon guiding 'deck' material, presently fibronectin is also present [3]. The end layer [2] may have an adjunct [4] which forms the device off ramp (e.g. haptotactic meso-material).

Rolling up of this composite as shown from the base (arrows & inset) automatically assembles the multiple meso-scale elements into the required spatial array (with overlaps, sequences, interfaces, spaces). It also has the major advantage (using thin layers) of converting 2D nano-layering technology for use in macro-devices with complex 3D spatial/directional organisation. Its development requires plotting and monitoring of spatial patterns formed at the nano-(electron microscope) level.

In Vivo Implantation

Spiral constructs were prepared by plastic compression, either with or without embedded rabbit tendon fibroblasts (allogeneic) as described above. Groups of PC implants were sutured between the intercostal muscle layers of rabbits and anchored between ribs, such that they were strained as the animal breathed. Implants were recovered after 1, 3, 5 weeks and where they were still in place and intact they were analysed histologically for amount and pattern of cell ingrowth, collagen deposition (birefringence), identification of inflammatory cells, capillary ingrowth. Capillary ingrowth was also monitored as haemoglobin and oxygenated haemoglobin levels at the time of sacrifice, using backscatter spectroscopic analysis, detecting the change in absorbance associated with (oxy)haemoglobin. Finally, recovered constructs were tested for changes in mechanical strength over time in vivo (as before on a DMA tensile testing instrument).

1 week cell in growth was modest in the cell free but greater in the cellular constructs, mainly over the surfaces and following short distances around the spirals into the deeper material. There was little sign of new collagen deposition and no vascular ingrowth.

3 week cellular constructs were visibly more vascularised with very little ingrowth into acellular constructs. Cell ingrowth was still greater for the cellular constructs and collagen deposition in the multi-cell layers, which over grew the outer and deeper inter-sheet spiral surfaces, was substantial. Direct participation of the seeded cells appeared to be minimal as they remained deep in the PC collagen material, yet all activity was histologically, consistently greater in cell-seeded than in cell free constructs.

5 weeks saw a further increase in the cell in growth to both types with a complete takeover of the construct cores in the cell-seeded versions. Cell free constructs were by this stage well-vascularised and much new collagen had been deposited between the spirals and over the surface in both types.

Figure 24:
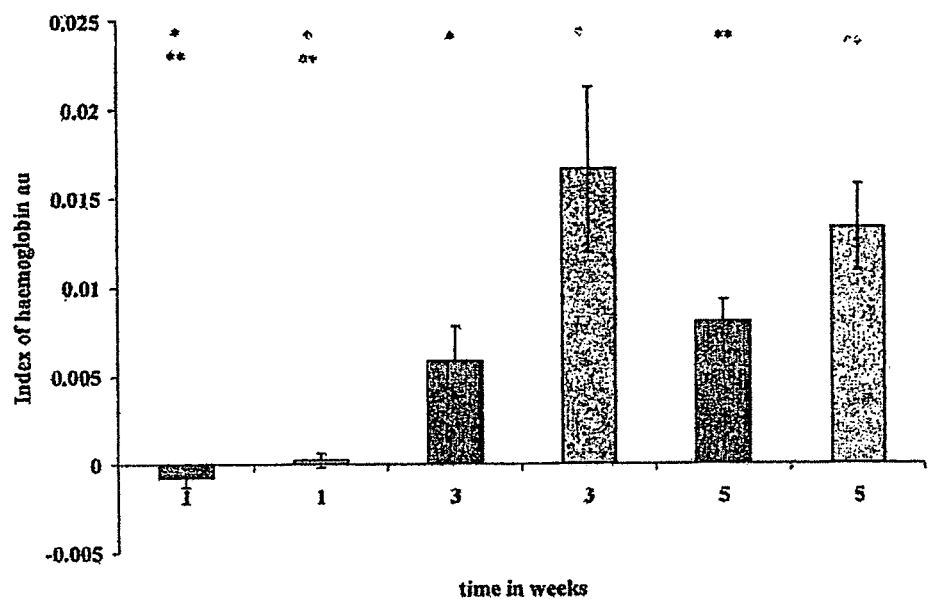
FIG. 24 shows the index of haemoglobin with implantation time for implants in vivo.

Backscatter spectroscopy showed a rapid increase in the haemoglobin index between 1 and 3 weeks, with ~3× greater at 3 weeks for cellular versus acellular construct (FIG. 24). Acellular construct caught up over the next 2 weeks. This indicates that the cell constructs were far more vascularised at 3 week than those without seeded cells.

Figure 25:
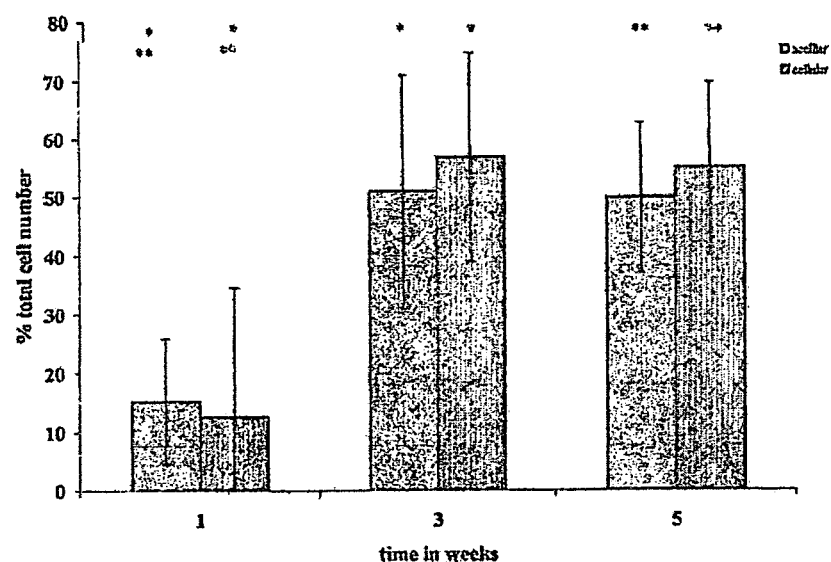
FIG. 25 shows the percentage of total cells that were CD31 positive in in vivo implants.
Figure 26:
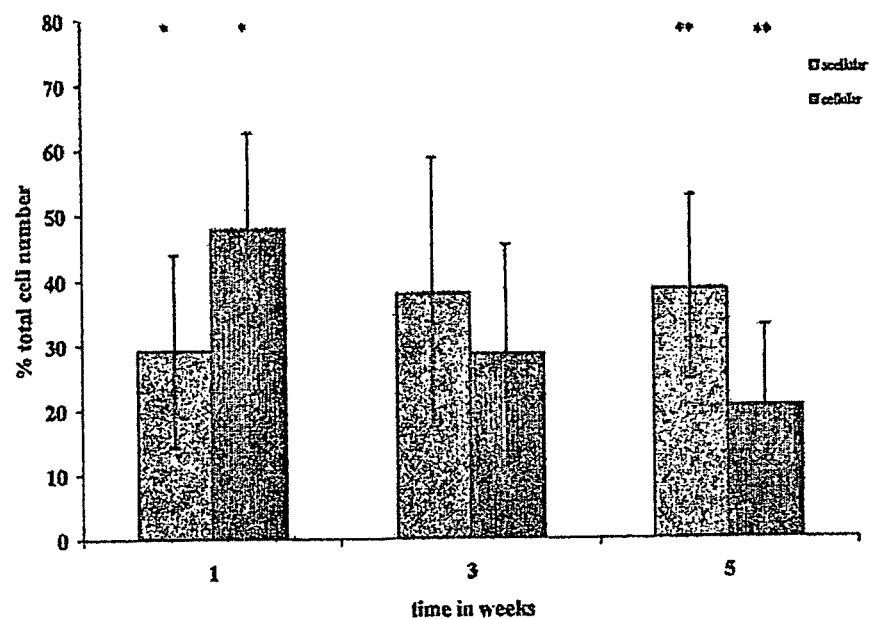
FIG. 26 shows the percentage of total cells that were CD45 positive in in vivo implants.
Figure 27:
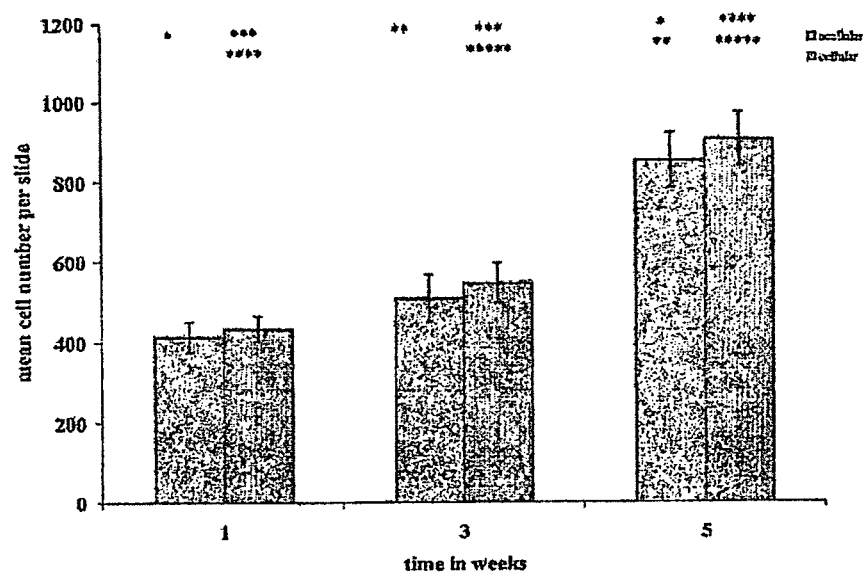
FIG. 27 shows the mean number of cells per slide in in vivo implants.

Infiltration of cells was quantitated and increased significantly at each time point, though the difference between the cell and non-cell types did not reach statistical significance. Cd31 staining increased in all constructs after 3 weeks (FIG. 25). % CD 45 leukocyte staining (FIG. 26) was relatively constant throughout. Total cell density increased slightly between 1 and 3 weeks (only significantly for cellular constructs) but rapidly between 3 and 5 weeks (>50% increase overall) (FIG. 27).

Figure 28:
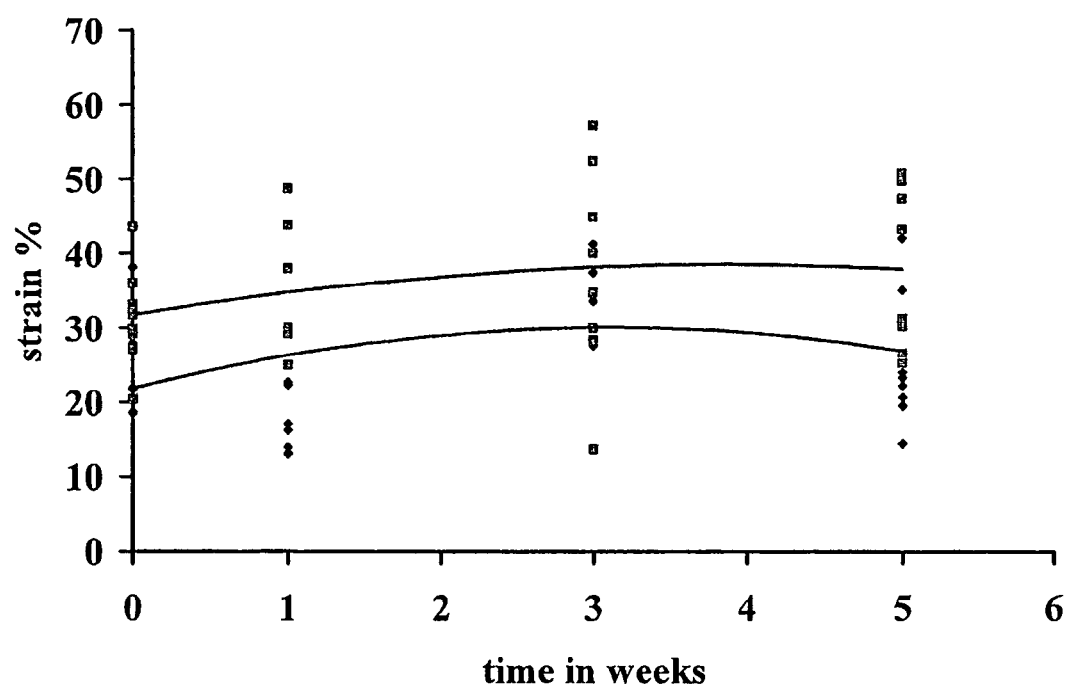
FIG. 28 shows the change in breaking strain from time 0 constructs with implantation. Acellular constructs are shown as dark diamonds and cellular constructs as light squares.
Figure 29:
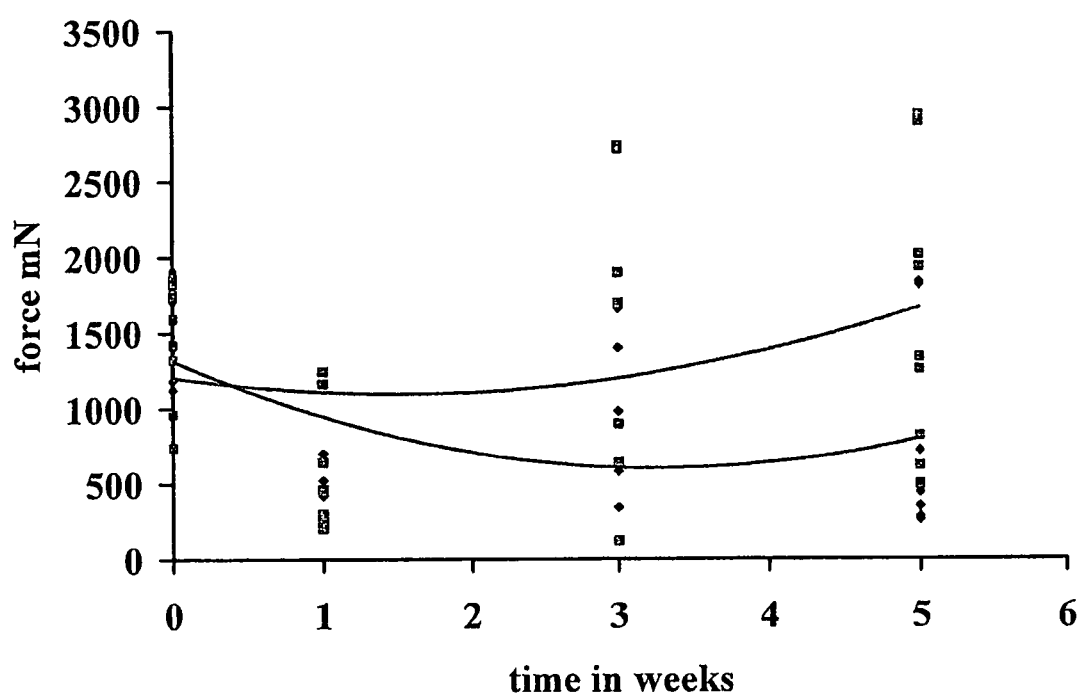
FIG. 29 shows the change in breaking force from time 0 constructs with implantation. Acellular constructs are shown as dark diamonds and cellular constructs as light squares.
Figure 30:
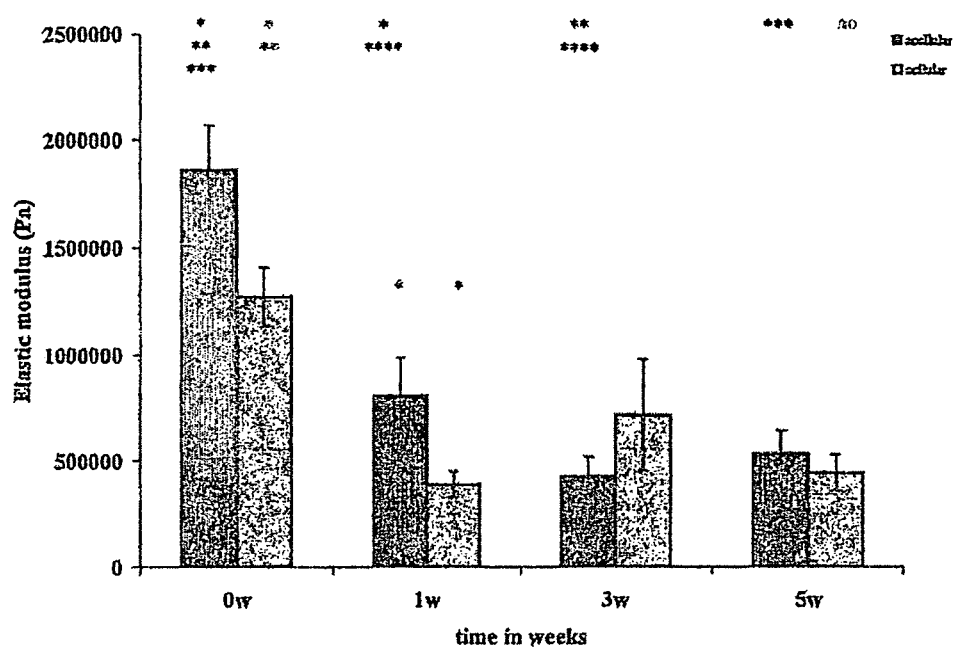
FIG. 30 shows the mean elastic modulus of in vivo implants.

Mechanical strength of the constructs was determined after recovery. The break stress of cell-free constructs fell initially over the first 3 weeks, then began to recover. In contrast, cellular constructs underwent no weakening and increased in strength between 3 and 5 weeks in vivo (FIG. 28). Overall strain to break was greater for cellular constructs and increased slightly (NS) over the implant period (FIG. 29). The elastic modulus was greater for acellular than cellular pre-implant constructs. This fell in all implanted constructs to 50% to 30% of pre implant values—i.e. implanted constructs became stiffer (FIG. 30).

Figure 31:
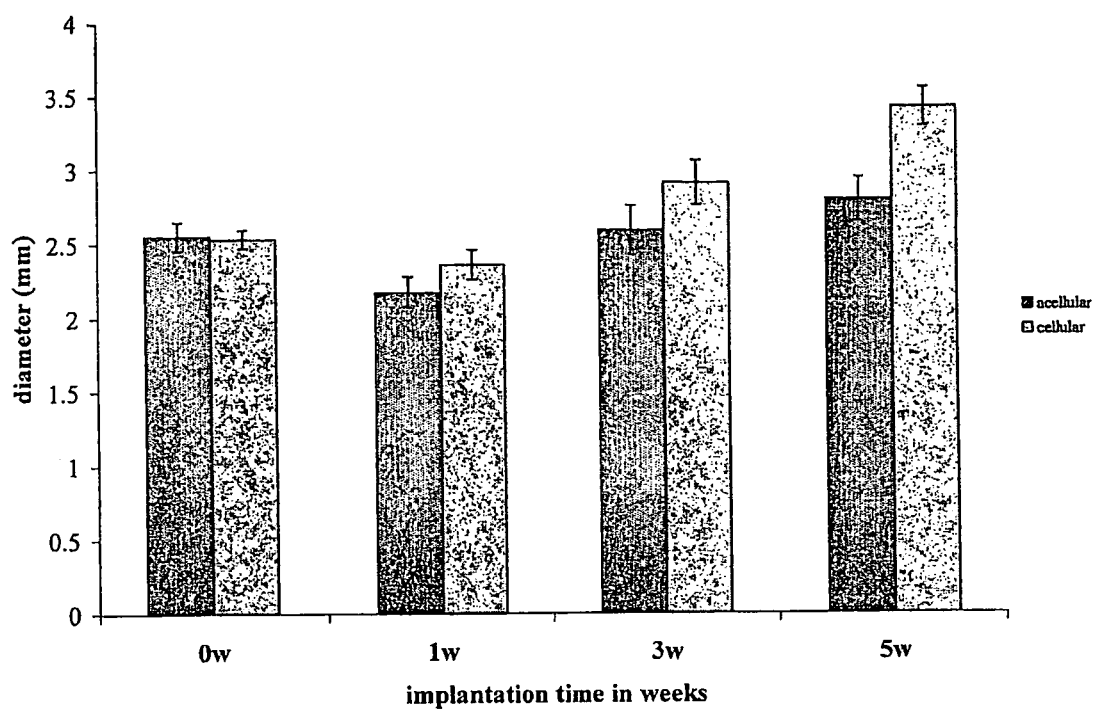
FIG. 31 shows the diameter of constructs as they were recovered after implantation (dark acellular, light cellular).

The cellular constructs increased significantly in diameter between 0 and 5 weeks, acellular constructs did not, and the cellular constructs at 5 weeks were significantly larger than the acellular constructs at the same point. Clearly, any initial loss of mass was at least replaced in both construct types (FIG. 31).

SUMMARY

Described herein is a radical new process to rapidly engineer neo-tissues or bioartificial materials, with controllable meso-scale structure. The simplicity and extreme rapidity of the process are its key features. The process will have immediate impact in a range of biomedical areas from tissue engineering, regeneration and reconstructive surgery to sustained drug delivery materials.

Plastic compaction (PC) fabrication generates reproducible and controllable structure with tensile properties approaching those of some native tissues. Structures are still many times weaker than the strongest tissues (e.g. ~100 MPa for tendon[15]) but can now be sutured and loaded in vivo for further remodelling. A further increase in mechanical properties could be produced by subjecting the rolled or folded constructs to a second compression, for example parallel to the long axis of a rolled construct. This controlled secondary compression, reducing the fluid content by up to a further 60%, was found to reproducibly increase the break stress by up to 100%.

Control of the mechanical properties of constructs is possible by selection of the compaction technique used and the extent (or stage) to which interstitial fluid is expelled. Stage 1 is seen with the mechanically fragile materials produced by slow fluid loss during auto-compression. Stage 2 is represented by the use of a single active compression and spiraling (50 g for 5 min) whilst a third stage can be achieved with a second compression, applied to the spiral itself. In practice the rapid, primary compression can be slowed down, for greater control of fluid removal and so the collagen sheet thickness, e.g. by compacting with the blotting layer only.

Meso-scale fabrication of structural features achieved through collagen lamella formation, surface topography, zoning and layering by spiral assembly addresses an urgent need to engineer localised biomimetic structures. For example this could be used to provide distinct ingrowth, through-growth and outgrowth structures for peripheral nerve regeneration (H. M. Geller et al *Exp. Neurol.* 2002, 174, 125). The two examples of spiral assembly shown herein represent a nerve regeneration template (collagen sheath and Fn neurite guidance core (J. Phillips et al *Biomaterials* 2003, 25, 2769) and a ligament model (collagen cable and hard tissue ends for anchorage).

In vitro constructs clearly underwent active remodelling, even in the simplest culture system and mechanical loading would further improve tensile properties. Cells assumed a tissue-like distribution and morphology, lining up along the many collagenous lamellae, with flattened spindle or discoid shapes. This channeling between collagen layers assists perfusion and enhances the tissue-like structure.

None of the constructs subjected to mechanical testing were tension pre-aligned and so collagen was essentially non-orientated in the X and Y planes (i.e. fibril orientation in lamellae was in the 'Z' plane) and this may have contributed to the relatively high compliance. Induction of X-Y fibril anisotropy produces materials with greater similarities to native tissues, particularly in terms of stiffness relative to the fibril alignment axis. In addition, break stress and yield stress for this study used cross-sectional areas measured on gross specimens. It is clear that the manual spiraling process left some channeling between the layers, implying that break strengths may have been underestimated. The finding that mechanical properties improved in culture demonstrates that the collagen matrix underwent natural cell remodelling, suggesting that constructs will integrate functionally in vivo.

The above experimental data shows that PC fabrication as described herein: (a) does not substantially reduce resident cell viability, (b) produces collagenous matrices with functional mechanical properties (strength and compliance), (c) can be predictably controlled to produce: (i) compositions with a complete range of cell- and matrix-densities, (ii) spatial/zonal heterogeneity and structural anisotropy appropriate for accurate biomimetic structures. The finding, (a), that relatively high fluid shear (i.e. >100 fold shrinkage in <5 min) is tolerated by resident fibroblasts shows that this process can be used for ultra-rapid fabrication, bypassing the current bottleneck in tissue fabrication. Production of matrices with tissue-like mechanical strength (b) means that constructs can be implanted directly or after brief culture. Furthermore, the ability to reproducibly limit the extent of compaction, as fluid expulsion, means that dimensions and mechanical properties are controllable. Poor tensile properties previously made suturing of collagen gels difficult or impossible without chemical cross-linking or reinforcement with other materials and so reduced mimicry of the native matrix.

Advantages of not requiring resident cell participation are: (i) potential for low temperature PC fabrication, minimising hypoxia and nutrient requirements; (ii) ability to position stem or progenitor cells within a tissue template before promoting differentiation, and (iii) production of acellular biomaterials with complex meso-scale structure (P. Vadgama et al., in Institute of Materials, Mineral and Mining, London (report number: FMP/03/01/IOM3), 2004, pp. 14-18). Other forms of hydrated gel, e.g. fibronectin, fibrin or synthetic polymers can be used to provide further meso-scale organisation. Further, such a process is amenable to large scale production or bedside 'individualised' fabrication.

TABLE 1

| | % weight (fluid)loss | | | |
|---|---|---|---|---|
| | 57% | 87% | 91% | 0% |
| Collagen Thickness | 229.0 (±14.0) µm (n = 20) | 48.2 (±8.7) µm (n = 20) | 21.8 (±5.3) µm (n = 20) | 3.6 (±0.22) mm (n = 20) |

TABLE 2

| | % Cell viability (+/−SD) | | | | |
|---|---|---|---|---|---|
| Cell Inoculum | Precompressed gel | Compressed only | Compressed + tensioned (20% strain) | Compressed plus 20s desiccation | Compressed plus 60s desiccation |
| 98.9 ± 0.25 | 95.0 ± 0.9 | 82.3 ± 2.3 | 86.2 ± 2.2 | 32.6 ± 30.0 | 0 0 |

REFERENCES

M. Eastwood et al Biophys. Biochim. Acta. 1994:1201; 186-192.
Eastwood M. et al J. Cell Physiol. 1996:166; 33-42.
Cacou C. et al Cell Eng. 1996:1:109-114.
Brown R A et al J. Cell Physiol 1996:169; 439-447.
Talas G. et al Int. J. Biochem. Cell Biol. 1997:29; 261-70.
Brown R A. et al J. Cell Physol. 1998:175; 323-32.
M. Eastwood et al Cell Motility Cytoskel. 1998:49; 13-21.
Eastwood M E et al J. Institute Mech. Eng. 1998. 212; 85-92.
R A. Porter et al Wound Repair Regen. 1998:6; 157-166.
Mudera V C. et al Cell Motility Cytoskel. 2000:45; 1-9.
Prajapati R T. et al. Wound Repair Regen. 2000:8; 227-238.
Parjapati R T. et al Wound Repair Regeneration. 2000:8; 239-247.
Brown R A. et al (2002) Exp. Cell Res. 274:310-322.
Sethi, K K et al (2002). Cell Motil. Cytoskel. 52: 231-241.
Cheema U. et al 2003. Cell Motil. Cytoskel. 54:226-236.
Sethi K K. et al. 2002. Wound Rep. Regen. 10; 397-408.
Brown R A. Next Generation Tissue Engineering: Clinical Applications and Mechanical Control. In 'Future Strategies for Tissue and Organ Replacement' (eds. Polak J M., Hench L L., Kemp P.). World Scientific Publishing, Singapore. (2002) 48-75.
Tomasek J J. et al (2002) Nature Reviews Molec. Cell Biol. 3:349-363.
Brown R A. et al Wound Rep. Regen. 1997:5; 212-21.
Krishnan L., Weiss J A, Wesserman M D, Hoying J B. (2004) Tissue Eng. 10:241-252
D. Huang et al, *Ann. Biomed. Eng.* 1993, 21, 289.
F. Volrath, D. P. Knight, *Nature* 2001, 410, 541.
Z. Feng, et al, *Artificial Organs* 2003, 27, 84
I. V. Yannas et al *Science* 1982, 215, 174.

S. F. Badylak, R et al *J. Biomed. Mater. Res.* 1995, 29, 977.
A. Curtis et al, *Arch. Dermatol.* 1998, 134, 293.
D. C. Wallace, J. Rosenblatt, *Adv. Drug Delivery Rev.* 2003, 55, 1631
Z. Rusczcak, W. Friess, *Adv. Drug Delivery Rev.* 2003, 55, 1679.
J. Garvin et al *Tissue Eng.* 2003, 9, 967.
S. Calve et al *Tissue. Eng.* 2004, 10, 755.
H. Schechtman, D. L. Bader. *J. Biomech.* 1997, 30, 829.
H. M. Geller, J. W. Fawcett, *Exp. Neurol.* 2002, 174, 125.
J. Phillips, R. A. Porter, Z. Ward, S. Standring, V. King, R. A. Brown, *Biomaterials* 2003, 25, 2769.
P. Vadgama et al. in Institute of Materials, Mineral and Mining,
London (report number: FMP/03/01/IOM3), 2004, 14-18.
A. M. Burt, D. A. McGrouther, in *Animal cell biotechnology*, Academic Press, New York 1994 p 150.
R. A. Brown et al *Biomaterials* 1994, 15, 457.
L. C. Junqueira, et al *Histochem J.* 1979, 11, 447.
A. R. Spurr, *J. Ultrastruct. Res.* 1969, 26, 31.
L. Wollweber et al *J. Microsc.* 1981, 121, 185

The invention claimed is:

1. A method of producing a biomaterial comprising viable mammalian cells, wherein the method comprises:
   providing a gel comprising a matrix of fibers and a liquid, said liquid being interstitial to the matrix of fibers, and the interstitial liquid containing viable mammalian cells, wherein said gel is produced by polymerisation of monomers dissolved in liquid containing viable mammalian cells; and,
   applying an external compaction to the gel to expel 50% to 99.9% of the interstitial liquid from the gel, thereby causing compaction of the gel,
   thereby producing a biomaterial comprising viable mammalian cells.

2. A method according to claim 1 wherein the gel is selected from the group consisting of silk gel, fibrin gel, fibronectin gel, elastin gel, collagen gel, chitin gel, and cellulose gel.

3. A method according to claim 1 wherein the gel is subjected to neither drying nor desiccation following the application of the external physical compaction.

4. A method according to claim 1 wherein the viable mammalian cells are selected from the group consisting of muscle cells, liver cells, kidney cells, heart cells, lung cells, gut cells, bronchial cells, ocular cells, reproductive cells, vascular cells, neural cells, secretory cells, stem cells, fibroblasts, Schwann cells, smooth muscle cells, endothelial cells, urothelial cells, osteocytes, chondrocytes, and tendon cells.

5. A method according to claim 1 wherein the cells are incubated in said gel for less than 6 hours before compaction.

6. A method according to claim 1 wherein gel has a cell density of at least $1 \times 10^4$ cells per ml before compaction.

7. A method according to claim 6 wherein the cell density is increased 5 to 200 fold by said compaction.

8. A method according to claim 1 wherein the gel is compacted over a period of less than 12 hours.

9. A method according to claim 8 wherein the gel is compacted over a period of less than 1 hour.

10. A method according to claim 1 wherein the gel is provided in an aqueous liquid, and said gel is immersed in the aqueous liquid during compaction.

11. A method according to claim 1 wherein the external compaction is applied by subjecting the gel to a mechanical force.

12. A method according to claim 11 wherein said mechanical force is a compressive force.

13. A method according to claim 12 wherein the compressive force is applied by centrifugation.

14. A method according to claim 1 wherein the external compaction is applied by subjecting the gel to one or more of draining, evaporation, suction, capillary pressure, osmosis or electro-osmosis.

15. A method according to claim 1 wherein the method comprises, before said external compaction is applied,
   applying tension to the gel in a first direction across the gel, such that the tension imparts a strain of 10-50% to the gel in the first direction and the fibers are aligned in the first direction.

16. A method according to claim 1 wherein said liquid containing said viable mammalian cells also contains capillary filaments,
   such that the gel comprises the viable mammalian cells and said capillary filaments.

17. A method according to claim 16 wherein the capillary filaments are soluble and dissolution of said filaments produces capillary channels in said biomaterial.

18. A method according to claim 1 wherein said liquid containing said viable mammalian cells also contains porous beads, such that said external compaction drives fibers of the matrix into pores of the porous beads.

19. A method according to claim 1 wherein said external compaction compresses the gel into a sheet of biomaterial comprising viable mammalian cells.

20. A method according to claim 19 further comprising rolling up said sheet of biomaterial comprising viable mammalian cells to form a roll.

21. A method according to claim 20 further comprising applying a second external compaction to said roll of biomaterial to expel interstitial liquid from said roll of biomaterial comprising viable mammalian cells.

22. A method according to claim 19 comprising folding up the said sheet of biomaterial to form a folded biomaterial comprising viable mammalian cells having two or more layers.

23. A method according to claim 22 further comprising applying a second external compaction to the folded biomaterial comprising viable mammalian cells to expel interstitial liquid from the folded biomaterial comprising viable mammalian cells.

24. A method according to claim 1 wherein the liquid is a cell culture medium containing viable mammalian cells.

25. A method according to claim 1 comprising storing said biomaterial comprising viable mammalian cells at 0 to 5° C.

26. A method according to claim 1 comprising implanting said biomaterial comprising viable mammalian cells in a human or animal body for the repair or replacement of damaged tissue.

27. A method of producing a biomaterial comprising viable mammalian cells according to claim 1 comprising prior to said application of the external compaction:
   folding the gel such that a first region of the gel overlays a second region of the gel,
   such that the application of said external compaction to said folded gel forms a sheet of biomaterial comprising viable mammalian cells, said sheet comprising two layers.

28. A method of producing a biomaterial comprising viable mammalian cells according to claim 1 comprising, prior to said application of the external physical compaction;

overlaying a second gel onto said gel,
wherein the second gel is produced by polymerisation of monomers dissolved in liquid to form a matrix of fibers and a liquid, said liquid being interstitial to the matrix of fibers,
such that the application of said external compaction to said gel and said second gel forms a sheet of biomaterial comprising viable mammalian cells, said sheet comprising two layers.

29. A method according to claim 28 further comprising overlaying one or more additional gels onto the second gel prior to said application of the external compaction, wherein the one or more additional gels are produced by polymerisation of monomers dissolved in liquid to form a matrix of fibers and a liquid, said liquid being interstitial to the matrix of fibers,
such that the application of said external compaction to said gel, said second gel and said one or more additional gels forms a sheet of biomaterial comprising viable mammalian cells, said sheet comprising said gel, said second gel and said one or more additional gels.

30. A method according to claim 29 wherein said gel, said second gel and said one or more additional gels differ according to one or more of the following characteristics: organisation of fibers in the gel, type of fibers in the gel and gel density.

31. A method according to claim 28 comprising folding up the sheet to form a folded biomaterial comprising viable mammalian cells.

32. A method according to claim 31 further comprising applying a second external compaction to the folded biomaterial to expel interstitial liquid from the folded biomaterial.

33. A method according to claim 28 comprising rolling up the sheet to form a roll of biomaterial comprising viable mammalian cells.

34. A method according to claim 33 further comprising applying a second external compaction to the roll of biomaterial comprising viable mammalian cells to expel interstitial liquid from the roll of biomaterial.

35. A method according to claim 28 further comprising moulding and/or shaping said biomaterial comprising viable mammalian cells during or after said application of the external compaction.

36. A method according to claim 28 wherein the interstitial liquid of the second gel is a cell culture medium and the second gel is produced by polymerisation of monomers dissolved in cell culture medium.

37. A method according to claim 28 wherein the interstitial liquid of the second gel comprises viable mammalian cells and the second gel is produced by polymerisation of monomers dissolved in liquid containing viable mammalian cells.

38. A method according to claim 37 wherein the viable mammalian cells are selected from the group consisting of muscle cells, liver cells, kidney cells, heart cells, lung cells, gut cells, bronchial cells, ocular cells, reproductive cells, vascular cells, neural cells, secretory cells, stem cells, fibroblasts, Schwann cells, smooth muscle cells, endothelial cells, urothelial cells, osteocytes, chondrocytes, and tendon cells.

39. A method of producing a biomaterial comprising viable mammalian cells, wherein the method comprises:

providing a gel comprising a matrix of fibers and a liquid, said liquid being interstitial to the matrix of fibers, and the interstitial liquid containing viable mammalian cells, wherein said gel is produced by polymerisation of monomers dissolved in liquid containing viable mammalian cells; and,
applying an external compaction to the gel to expel 50% to 99.9% of the interstitial liquid from the gel, thereby causing compaction of the gel,
thereby producing a biomaterial comprising viable mammalian cells,
wherein the gel is not dried or desiccated following the application of the external compaction and the cells remain viable when the gel is compacted.

* * * * *